(12) United States Patent
Blurton

(10) Patent No.: US 10,080,520 B2
(45) Date of Patent: Sep. 25, 2018

(54) LABOR MONITORING OF PELVIC FLOOR

(71) Applicant: Stetrix, Inc., Oakland, TN (US)

(72) Inventor: David D. Blurton, Whiteville, TN (US)

(73) Assignee: Stetrix, Inc., Oakland, TN (US)

( * ) Notice: Subject to any disclaimer, the term of this patent is extended or adjusted under 35 U.S.C. 154(b) by 235 days.

(21) Appl. No.: 15/054,987

(22) Filed: Feb. 26, 2016

(65) Prior Publication Data
US 2016/0249848 A1 Sep. 1, 2016

Related U.S. Application Data

(60) Provisional application No. 62/121,580, filed on Feb. 27, 2015.

(51) Int. Cl.
| | |
|---|---|
| *A61B 5/00* | (2006.01) |
| *A61B 5/0488* | (2006.01) |
| *A61B 5/0492* | (2006.01) |

(52) U.S. Cl.
CPC .......... *A61B 5/4343* (2013.01); *A61B 5/0492* (2013.01); *A61B 5/04882* (2013.01); *A61B 5/4356* (2013.01); *A61B 5/7455* (2013.01); *A61B 2562/0261* (2013.01); *A61B 2562/046* (2013.01); *A61B 2562/164* (2013.01)

(58) Field of Classification Search
CPC ............................ A61B 5/4343; A61B 5/4356
See application file for complete search history.

(56) References Cited

U.S. PATENT DOCUMENTS

| | | |
|---|---|---|
| 1,511 A | 3/1840 | Truss |
| 316,903 A | 4/1885 | Lytle |
| 412,999 A | 10/1889 | Turney |
| 453,880 A | 6/1891 | Coffee |
| 504,598 A | 9/1893 | Leyda |

(Continued)

FOREIGN PATENT DOCUMENTS

| | | |
|---|---|---|
| CA | 2024655 A1 | 3/1992 |
| CH | 337982 A | 4/1959 |

(Continued)

OTHER PUBLICATIONS

Sharp, U.S. Appl. No. 60/744,017, filed Mar. 31, 2006.
(Continued)

*Primary Examiner* — Eric D. Bertram
(74) *Attorney, Agent, or Firm* — Haynes and Boone, LLP

(57) ABSTRACT

The present disclosure provides devices that noninvasively monitor the activity of pelvic floor muscles during labor, and in embodiments also provides perivaginal tissue support. electrode sensors are applied to perivaginal tissue and, in embodiments, a perivaginal support device during labor. The electrode signals are analyzed to estimate an efficacy of voluntary pushing and the efficacy is used, at least in part, to predict a success of vaginal birth. A pressure detection system may also be included with the perivaginal support device to detect pressure indicative of pressure on the perivaginal tissue of a patient, which may be modified to prevent tissue damage to the patient. The incidence of Cesarean childbirth may be reduced by managing the labor process in this manner. In one aspect, a tactile feedback device is positioned adjacent the perivaginal tissues.

20 Claims, 13 Drawing Sheets

(56) References Cited

U.S. PATENT DOCUMENTS

| | | | |
|---|---|---|---|
| 572,465 A | 12/1896 | Woolfolk et al. |
| 798,367 A | 8/1905 | Smokey |
| 800,071 A | 9/1905 | Cheatham |
| 811,167 A | 1/1906 | Paddock |
| 930,768 A | 8/1909 | Kelly |
| 933,610 A | 9/1909 | Yanowsky |
| 940,576 A | 11/1909 | Barnes |
| 942,590 A | 12/1909 | Sanborn |
| 964,309 A | 7/1910 | Parrott |
| 969,134 A | 8/1910 | Cowie |
| 1,031,841 A | 7/1912 | Eblen |
| 1,195,931 A | 8/1916 | Sowell |
| 1,228,384 A | 6/1917 | Agerton |
| 1,249,195 A | 12/1917 | Raines |
| 1,463,177 A | 7/1923 | Scholz |
| 1,529,937 A | 3/1925 | Turcotte |
| 1,543,632 A | 6/1925 | Louis |
| 1,547,127 A | 7/1925 | Metzger |
| 1,565,808 A | 12/1925 | Levy |
| 1,711,294 A | 4/1929 | Weitzner |
| 1,877,766 A | 9/1932 | Kennedy |
| 1,983,636 A | 12/1934 | Palkens |
| 2,009,655 A | 7/1935 | Freymann |
| 2,073,094 A | 3/1937 | Bugh |
| 2,104,699 A | 1/1938 | O'Dell |
| 2,128,670 A | 8/1938 | Bolder |
| 2,282,021 A | 5/1942 | Benningfield |
| 2,327,671 A | 8/1943 | Rupprecht |
| 2,468,348 A | 4/1949 | Shore |
| 2,597,637 A | 5/1952 | Hermann |
| 2,653,599 A | 9/1953 | Bell |
| 2,672,862 A | 3/1954 | Krauss |
| 2,719,568 A | 10/1955 | Webb |
| 2,840,822 A | 7/1958 | Ericsson |
| 2,981,255 A | 4/1961 | Heyns |
| 3,101,718 A | 8/1963 | Rocker |
| 3,103,316 A | 9/1963 | Schaal |
| 3,116,735 A | 1/1964 | Geimer |
| 3,207,160 A | 9/1965 | Heyns |
| 3,216,423 A | 11/1965 | Blonsky et al. |
| 3,452,362 A | 7/1969 | Korolick et al. |
| 3,554,190 A | 1/1971 | Kaplan |
| 3,712,300 A | 1/1973 | Davidowitz |
| 3,789,657 A | 2/1974 | Ching et al. |
| 3,826,242 A | 7/1974 | Eggers |
| 3,939,842 A | 2/1976 | Harris |
| 4,213,463 A | 7/1980 | Osenkarski |
| 4,239,037 A | 12/1980 | Fausone |
| 4,240,436 A | 12/1980 | Singleton |
| 4,263,914 A | 4/1981 | Pawlak |
| 4,270,541 A | 6/1981 | Okamoto et al. |
| 4,319,583 A | 3/1982 | Ingle |
| 1,139,180 A | 12/1982 | Kline |
| 4,365,631 A | 12/1982 | Kline |
| 4,421,504 A | 12/1983 | Kline |
| 1,145,899 A | 5/1984 | Bond |
| 4,484,919 A | 11/1984 | Sohn et al. |
| 4,530,122 A | 7/1985 | Sanders et al. |
| 4,557,260 A | 12/1985 | Reyes, Jr. |
| 4,583,542 A | 4/1986 | Boyd |
| 4,624,258 A | 11/1986 | Stubbs |
| 4,638,806 A | 1/1987 | Bartlett |
| 4,670,419 A | 6/1987 | Uda et al. |
| 4,691,333 A | 9/1987 | Gabriele et al. |
| 4,706,661 A | 11/1987 | Barrett |
| 4,732,146 A | 3/1988 | Fasline et al. |
| 4,782,535 A | 11/1988 | Yewer, Jr. et al. |
| 4,790,314 A | 12/1988 | Weaver |
| 4,794,915 A | 1/1989 | Larsson |
| 4,817,625 A | 4/1989 | Miles |
| 4,822,317 A | 4/1989 | Wimmer |
| 4,825,866 A | 5/1989 | Pierce |
| 4,866,789 A | 9/1989 | Dorm |
| 4,891,847 A | 1/1990 | Baker et al. |
| 4,976,692 A | 12/1990 | Atad |
| 4,981,307 A | 1/1991 | Walsh |
| 4,995,383 A | 2/1991 | Anderson |
| 5,007,412 A | 4/1991 | DeWall |
| 5,040,524 A | 8/1991 | Votel et al. |
| 5,099,702 A | 3/1992 | French |
| 5,148,549 A | 9/1992 | Sydor |
| 5,154,177 A * | 10/1992 | Eisman .............. A61B 5/0492 |
| | | 600/373 |
| 5,174,281 A | 12/1992 | Lee |
| 5,178,627 A | 1/1993 | Hudock |
| 5,234,462 A | 8/1993 | Pavletic |
| 5,263,926 A | 11/1993 | Wilk |
| 5,395,301 A | 3/1995 | Russek |
| 5,405,356 A | 4/1995 | Hahn et al. |
| 5,432,951 A | 7/1995 | Yewer, Jr. |
| 5,493,735 A | 2/1996 | Rice |
| 5,569,165 A | 10/1996 | Chin et al. |
| 5,652,395 A | 7/1997 | Hirano et al. |
| 5,676,637 A | 10/1997 | Lee |
| 5,690,607 A | 11/1997 | Chin et al. |
| 5,695,484 A | 12/1997 | Cox |
| 5,704,894 A | 1/1998 | Boutos |
| 5,709,650 A | 1/1998 | Colman |
| 5,800,485 A | 9/1998 | Trop et al. |
| 5,843,025 A | 12/1998 | Shaari |
| 5,908,379 A | 1/1999 | Schaefer et al. |
| 5,924,423 A | 7/1999 | Majlessi |
| 5,928,059 A | 7/1999 | Wicks |
| 5,935,595 A | 8/1999 | Steen |
| 5,991,979 A | 11/1999 | Moore et al. |
| 6,071,175 A | 6/2000 | Working, III |
| 6,083,241 A | 7/2000 | Longo et al. |
| 6,102,271 A | 8/2000 | Longo et al. |
| 6,123,667 A | 9/2000 | Poff et al. |
| 6,142,933 A | 11/2000 | Longo et al. |
| 6,146,345 A | 11/2000 | Mignard |
| 6,159,070 A | 12/2000 | Schwartz et al. |
| D437,642 S | 2/2001 | Caballero |
| 6,364,852 B1 | 4/2002 | Lee |
| 6,428,004 B1 | 8/2002 | McQuitty et al. |
| 6,503,192 B1 | 1/2003 | Ouchi |
| 6,517,562 B1 | 2/2003 | Holland |
| 6,537,132 B1 | 3/2003 | Alberts |
| 6,572,541 B1 | 6/2003 | Petersvik |
| 6,623,588 B1 | 9/2003 | Rasmussen |
| 6,627,632 B2 | 9/2003 | Parks et al. |
| 6,648,842 B2 | 11/2003 | Horkel |
| 6,668,833 B2 | 12/2003 | Rhee |
| 6,710,099 B2 | 3/2004 | Cinelli et al. |
| 6,712,841 B2 | 3/2004 | Gomez |
| 6,716,229 B2 | 4/2004 | Toth |
| 6,913,573 B1 | 7/2005 | Viscomi et al. |
| 6,916,494 B2 | 7/2005 | Park |
| 6,991,813 B2 | 1/2006 | Xu |
| 7,144,379 B2 | 12/2006 | Belli |
| 7,160,294 B2 | 1/2007 | Croft |
| 7,198,609 B2 | 4/2007 | Rolnick |
| 7,318,810 B1 | 1/2008 | Benson |
| 7,673,633 B2 | 3/2010 | Blurton et al. |
| 7,730,846 B2 | 6/2010 | Pett et al. |
| 7,766,931 B2 | 8/2010 | Blurton |
| 7,850,625 B2 | 12/2010 | Paltieli et al. |
| 8,062,277 B2 | 11/2011 | Fleming |
| 8,066,009 B2 | 11/2011 | Blurton et al. |
| 8,123,760 B2 | 2/2012 | Blurton |
| 8,277,427 B2 | 10/2012 | Edvardsen et al. |
| 8,353,884 B2 | 1/2013 | Hansen et al. |
| 8,407,824 B2 | 4/2013 | Springer |
| 8,449,481 B2 | 5/2013 | Rohde et al. |
| 8,597,306 B1 * | 12/2013 | Blurton .............. A61B 17/42 |
| | | 600/588 |
| 8,672,910 B1 | 3/2014 | Kaufman |
| 2001/0000731 A1 | 5/2001 | Jia et al. |
| 2001/0003157 A1 | 6/2001 | Toth |
| 2002/0072522 A1 | 6/2002 | Parks et al. |
| 2002/0129658 A1 | 9/2002 | Rider |
| 2002/0142902 A1 | 10/2002 | Stein |
| 2002/0147482 A1 | 10/2002 | Carter |
| 2002/0187990 A1 | 12/2002 | Parks et al. |

(56) References Cited

U.S. PATENT DOCUMENTS

| | | | |
|---|---|---|---|
| 2002/0192273 | A1 | 12/2002 | Buseman et al. |
| 2003/0021850 | A1 | 1/2003 | Xu |
| 2003/0092969 | A1 | 5/2003 | O'Malley et al. |
| 2003/0109905 | A1 | 6/2003 | Mok et al. |
| 2003/0229263 | A1 | 12/2003 | Connors et al. |
| 2003/0236442 | A1 | 12/2003 | Connors et al. |
| 2004/0067716 | A1 | 4/2004 | Wakefield |
| 2004/0076688 | A1 | 4/2004 | Park |
| 2004/0088031 | A1 | 5/2004 | Gomez |
| 2004/0186356 | A1 | 9/2004 | O'Malley et al. |
| 2004/0217146 | A1 | 11/2004 | Beck |
| 2004/0254590 | A1 | 12/2004 | Hoffman et al. |
| 2005/0000003 | A1 | 1/2005 | Bushelman |
| 2005/0049509 | A1 | 3/2005 | Mansour et al. |
| 2005/0049660 | A1 | 3/2005 | Croft |
| 2005/0192169 | A1 | 9/2005 | Girgen et al. |
| 2005/0203565 | A1 | 9/2005 | Rethy et al. |
| 2005/0204455 | A1 | 9/2005 | Pelligra |
| 2005/0214327 | A1 | 9/2005 | Brooks et al. |
| 2006/0025766 | A1 | 2/2006 | Heinrich et al. |
| 2006/0058831 | A1 | 3/2006 | Atad |
| 2006/0144897 | A1 | 7/2006 | Jankowski et al. |
| 2006/0149177 | A1 | 7/2006 | Root et al. |
| 2006/0153927 | A1 | 7/2006 | Xu |
| 2006/0155340 | A1 | 7/2006 | Schuler et al. |
| 2006/0180158 | A1 | 8/2006 | McKnight et al. |
| 2006/0195146 | A1 | 8/2006 | Tracey et al. |
| 2006/0195153 | A1 | 8/2006 | DiUbaldi et al. |
| 2006/0198883 | A1 | 9/2006 | Parks et al. |
| 2006/0200187 | A1 | 9/2006 | Gude |
| 2006/0282019 | A1 | 12/2006 | Hamilton |
| 2007/0011802 | A1 | 1/2007 | Holland |
| 2007/0232864 | A1 | 10/2007 | Sharp et al. |
| 2008/0027357 | A1 | 1/2008 | Owen |
| 2009/0076337 | A1 | 3/2009 | Yang et al. |
| 2009/0314097 | A1 | 12/2009 | Cairo et al. |
| 2010/0292615 | A1 | 11/2010 | Niederberger |
| 2011/0022056 | A1 | 1/2011 | Haadem |
| 2011/0112403 | A1* | 5/2011 | Machtey ............ A61B 8/02 600/443 |
| 2011/0144458 | A1* | 6/2011 | Gauta ............ A61B 5/033 600/304 |
| 2011/0190652 | A1* | 8/2011 | Fink ............ A61B 5/4325 600/546 |
| 2011/0237972 | A1* | 9/2011 | Garfield ............ A61B 5/04882 600/546 |
| 2011/0251512 | A1* | 10/2011 | Fink ............ A61B 5/0488 600/546 |
| 2012/0053535 | A1 | 3/2012 | Blurton et al. |
| 2012/0083798 | A1 | 4/2012 | Belli |
| 2012/0109028 | A1 | 5/2012 | Sheffield |
| 2012/0221012 | A1 | 8/2012 | Blurton |
| 2012/0245490 | A1* | 9/2012 | Fausett ............ A61B 5/11 600/595 |
| 2013/0053863 | A1 | 2/2013 | Juravic et al. |

FOREIGN PATENT DOCUMENTS

| | | |
|---|---|---|
| CN | 2054668 U | 3/1990 |
| CN | 2083038 U | 8/1991 |
| CN | 1055107 A | 10/1991 |
| CN | 2097619 U | 3/1992 |
| CN | 2115081 U | 9/1992 |
| CN | 2217960 Y | 1/1996 |
| CN | 2253637 Y | 5/1997 |
| CN | 2335578 Y | 9/1999 |
| CN | 2336759 Y | 9/1999 |
| CN | 2340385 Y | 9/1999 |
| CN | 2467063 Y | 12/2001 |
| CN | 2516111 Y | 10/2002 |
| CN | 2538288 Y | 3/2003 |
| CN | 2873115 Y | 2/2007 |
| CN | 2897180 Y | 5/2007 |
| CN | 2933318 Y | 8/2007 |
| CN | 200977195 Y | 11/2007 |
| CN | 200980714 Y | 11/2007 |
| CN | 201064475 Y | 5/2008 |
| CN | 201108483 Y | 9/2008 |
| CN | 201168018 Y | 12/2008 |
| CN | 201197732 Y | 2/2009 |
| CN | 101554337 A | 10/2009 |
| CN | 201333088 Y | 10/2009 |
| CN | 201394058 Y | 2/2010 |
| CN | 201492488 U | 6/2010 |
| CN | 201529140 U | 7/2010 |
| CN | 201564577 U | 9/2010 |
| CN | 201668476 U | 12/2010 |
| CN | 201734761 U | 2/2011 |
| CN | 201734762 U | 2/2011 |
| CN | 201949105 U | 8/2011 |
| CN | 202015251 U | 10/2011 |
| CN | 202027688 U | 11/2011 |
| CN | 202136401 U | 2/2012 |
| CN | 202154729 U | 3/2012 |
| CN | 202207192 U | 5/2012 |
| CN | 202409090 U | 9/2012 |
| CN | 202409091 U | 9/2012 |
| CN | 202437308 U | 9/2012 |
| CN | 202505460 U | 10/2012 |
| CN | 202637069 U | 1/2013 |
| CN | 102988102 A | 3/2013 |
| CN | 202942188 U | 5/2013 |
| CN | 202982169 U | 6/2013 |
| DE | 2739589 A1 | 3/1979 |
| DE | 202009001363 U1 | 5/2009 |
| EP | 1477197 | 11/2004 |
| GB | 1127548 A | 9/1968 |
| GB | 2288023 A | 10/1995 |
| JP | 7275309 | 10/1995 |
| JP | 2001129004 | 5/2001 |
| JP | 2001170093 | 6/2001 |
| RU | 2196491 | 1/2003 |
| WO | WO9629013 | 9/1996 |
| WO | WO9932003 | 7/1999 |
| WO | WO2001041630 A2 | 6/2001 |
| WO | WO0213680 A2 | 2/2002 |
| WO | WO03053255 A1 | 7/2003 |
| WO | WO2006086785 | 8/2006 |
| WO | WO2007114982 | 10/2007 |
| WO | WO2008096953 A1 | 8/2008 |
| WO | WO2009110863 A1 | 9/2009 |
| WO | WO2011072736 A1 | 6/2011 |

OTHER PUBLICATIONS

Bryant Ruth A., "Saving the Skin From Tape Injuries", Reprinted from American Journal of Nursing, Feb. 1988, vol. 88, No. 2, 3 pages.
Dykes et al., "Effects of Adhesive Dressings on the Stratum Corneum of the Skin", Journal of Wound Care, vol. 10, No. 2 Feb. 2001, pp. 1-4.
Gerhardt, et al., "Study of Skin-Fabric Interactions of Relevance to Decubitus: Friction and Contact-Pressure Measurements", Skin Research and Technology, 2008, 14, pp. 77-88, printed in Singapore.
Goossens, et al., "Decubitus Risk: Is Shear More Important Than Pressure?" Proceedings of the IEA 2000/HFES 2000 Congress, pp. 4-700-4-703.
Harahap Marwali, p. 19 of the book entitled: "Surgical Techniques for Cutaneous Scar Revision", 1 page.
Jacquet et al., "A New Experimental Method for Measuring Skin's Natural Tension", Skin Research and Technology 2008; 14: pp. 1-7, printed in Singapore.
Karwoski et al., "Experiments on Peeling Adhesive Tapes from Human Forearms", Skin Research and Technology 2004; 10: pp. 271-277, printed in Denmark.
Koval et al., "Tape Blisters Following Hip Surgery", A Prospective, Randomized Study of Two Types of Tape, Investigation performed at The Hospital for Joint Diseases, New York, and Jamaica Hospital Medical Center, Jamaica, New York, pp. 1884-1887, The Journal of Bone and Joint Surgery, Inc.

(56) References Cited

OTHER PUBLICATIONS

Lippmann et al., "An Alternative Anesthetic Technique for the Morbidly Obese Patient Undergoing Endovascular Repair of an Abdominal Aortic Aneurysm", From the Departments of Anesthesiology and Surgery, Harbor-UCLA Medical Center, Torrance, CA, Anesth Analg 2003;97, pp. 981-983.
Loerakker, Sandra, "Aetiology of Pressure Ulcers", Eindhoven University of Technology, Dept. of Biomedical Engineering, Section Materials Technology, Div. Biomechanics and Tissue Engineering, Oct. 2007, 31 pages.
Murahata, et. al., "Preliminary Studies on the Relationship Among Peel Force, Quantitative Measures of Skin Damage and Subjective Discomfort", Skin Research and Technology 2008; 14: pp. 1-6, printed in Singapore.
Ohura et al., "Influence of External Forces (Pressure and Shear Force) on Superficial Layer and Subcutis of Porcine Skin and Effects of Dressing Materials: Are Dressing Materials Beneficial for Reducing Pressure and Shear Force in Tissues?" Wound Repair and Regeneration (2008); 16, pp. 102-107.
Sarifakioglu et al., "Dressing Spray Enhances the Adhesive Strength of Surgical Dressing Tapes", Indian Journal of Dermatology, Venereology and Leprology, printed from www.ijdvl.com/article.asp?issn=0378-6323;year=2006;vol.72;issue=5;epage=353;epage=356, on Apr. 16, 2008, pp. 1-5.
Thomas Steve, "World Wide Wounds—Atraumatic Dressings", Published Jan. 2003, printed from www.worldwidewounds.com/2003/january/Thomas/Atraumatic-Dressings.html on Jan. 22, 2009, pp. 1-10.
Viegas et al., "Preventing a Surgical Complication During Cesarean Delivery in a Morbidly Obese Patient: A Simple Apparatus to Retract the Abdominal Panniculus", MedGenMed Ob/Gyn & Women's Health, Medscape General Medicine, 2006;8(1):52 printed from www.medscape.com/viewarticle/518147_print, on Nov. 16, 2007, pp. 1-5.
Wang et al., "In Vivo Biomechanics of the Fingerpad Skin Under Local Tangential Traction", Journal of Biomechanics, 2007, 40(4):851-860.
Breast Forms printed from www.geocities.com/KarenSpecial/bustform.html on Jan. 9, 2008, pp. 1-11.
Canica, Dynamic Wound Stabilization, "SutureSafe" printed from www.canica.com/suturesafe.asp on Feb. 14, 2008, 2 pages.
Max-Support Abdominal Retraction Belt by Vascular Solutions, Brochure, pp. 1-4.
FLEXcon Providing Solutions in Pressure Sensitive Films, Product Construction Sheet, 1 page.

3M Preliminary Technical Information Sheet, 3M Gamma Stable Medical Fastener, #7333, Gamma Stable Hook Fastener with Adhesive, 2 pages.
3M Preliminary Technical Information Sheet, 3M Gamma Stable Medical Fastener, #7331, Gamma Stable Loop Fastener with Adhesive, 2 pages.
3M Health Care 2005, "Reducing the Risk of Superficial Skin Damage Related to Adhesive Use", 2 pages.
Vascular Solutions Bringing Solutions to Vascular Medicine, "Max-Support Abdominal Retraction Belt", printed from www.vascularsolutions.com/products/max-support on Jan. 2, 2008, 1 page.
Abramowitz et al., "Epidemiology of anal lesions (fissure and thrombosed external hemorrhoid) during pregnancy and postpartum", Gynecol Obstet Fertil 2003, No. 31, 546-549.
Danel, "Magnitude of Maternal Morbidity During Labor and Delivery: United States, 1993-1997", American Journal of Public Health, Apr. 2003, vol. 93, No. 4, pp. 631-634.
International Search Report of the International Searching Authority for PCT/US06/29583 dated Aug. 3, 2007, 2 pages.
International Search Report and Written Opinion of the International Searching Authority for PCT/US2007/068143 dated Sep. 4, 2008, 11 pages.
Madoff, Robert, et al., "American Gastroenterological Association Technical Review on the Diagnosis and Treatment of Hemorrhoids," American gastroenterological Association Clinical Practice Committee, Jan. 8, 2004, gastroenterology 2004; 126:1463-1473.
Dimmer, Christine, et al., "Squatting for the Prevention of Hemorrhoids?" Department of Science and Technology Studies, University of Wollongong, NSW 2522, Australia, Townsend Letter for Doctors & Patients, Issue No. 159, Oct. 1996, pp. 66-70, http://www.uow.edu.au/arats/sts/bmartin/pubs/96tldp.html, 18 pages.
Agency for Healthcare Research and Quality, "Strategies to Reduce Cesarean Birth in Low-Risk Women" Comparative Effectiveness Review No. 80, Pub. No. 12(13)-EHC 128-1, Oct. 2012, 15 pages.
International Search Report and Written Opinion issued for PCT/US2014/021965 dated Jun. 3, 2014, 14 pages.
International Preliminary Report on Patentability issued for PCT/US2014/021965 dated Sep. 24, 2015, 10 pgs.
Masahiro Takano, Anal Diseases, Pregnancy and Parturition, 1990, Nippon Daicho Komonbyo Gakkai Zasshi, Takyo, 1990; 43(6); pp. 1077-1082; with English translation, 64 pages.
European Office Action dated Jul. 25, 2016 in connection with European Patent Application No. 06788889.1; 4 pp.

* cited by examiner

LABOR MONITORING OF PELVIC FLOOR

INCORPORATION BY REFERENCE

This application claims priority to U.S. Provisional Application No. 62/121,580 filed Feb. 27, 2015. The following are commonly assigned with the present application: U.S. patent application Ser. No. 14/529,235, filed Oct. 31, 2014, is a continuation of U.S. patent application Ser. No. 14/195,070, filed Mar. 3, 2014, issued as U.S. Pat. No. 8,888,719 on Nov. 11, 2014, which is a continuation of U.S. patent application Ser. No. 13/833,189, filed Mar. 15, 2013, issued as U.S. Pat. No. 8,684,954 on Apr. 1, 2014, which claims priority to and the benefit of the filing date of U.S. Provisional Patent Application 61/782,814 filed Mar. 14, 2013. These are all incorporated herein by reference in their entireties.

BACKGROUND

In modern times, there has been a dramatic increase in the incidence of children born by Cesarean childbirth. This form of child birth significantly increases the cost to the healthcare system when compared to a natural vaginal delivery. In addition, the birthing mother needs significantly more time to recover from a Cesarean operation compared to a natural vaginal delivery. One cause attributed to this rise is the use of epidurals and pain relieving drugs during the labor and delivery process, which can desensitize the birthing mother from experiencing the natural body signals needed to push the baby through the birth canal and thereby ultimately delay the progression of childbirth.

Numerous labor monitoring practices have been implemented in attempts to monitor and manage the process of labor, including observing maternal and fetal heart rates, respiration, blood pressure, temperature, as well as the frequency and strength of uterine contractions. Specifically, intrapartum assessment of uterine activity has been used to first monitor labor progress and, second, to identify unsuccessful labor that results in Cesarean delivery. These intrapartum assessments, however, have focused on either non-invasive tools at the abdomen or invasive tools for vaginal wall, cervix, or intrauterine measurements. Non-invasive tools have included tocodynamometers and electromyography (EMG) electrodes placed at a location at the mother's abdomen during labor, while invasive tools have included intrauterine pressure catheters.

The current use of non-invasive tools, such as EMG electrodes at the abdomen of the mother, has been limited to measuring electrical activity of the uterus of the mother at rest and during contractions. Yet other factors also influence the probability of successful vaginal birth beyond contractions, including pelvic girth, child head size, and voluntary pushing forces. It has been estimated, for example, that voluntary pushing forces (exerted by the mother) may account for up to 30% of the expulsive force necessary to push the child from the birth canal. As a voluntary pushing force, the mother has a degree of control over how much and when it is applied. However, epidurals and pain relieving drugs may desensitize the mother to signals indicating that more force, or less, should be applied in voluntary pushing.

There are no currently available devices and methods that permit a healthcare provider to actively manage the labor and birthing process by monitoring pelvic floor activity to promote a higher incidence of vaginal births and, if desired in certain situations, manage the labor process to avoid potential damage to the mother such as pelvic floor injuries and anal sphincter damage. Thus, there is a need for devices and methods permitting the management of the child birthing process by monitoring pelvic floor activity.

DETAILED DESCRIPTION

Figure 1:
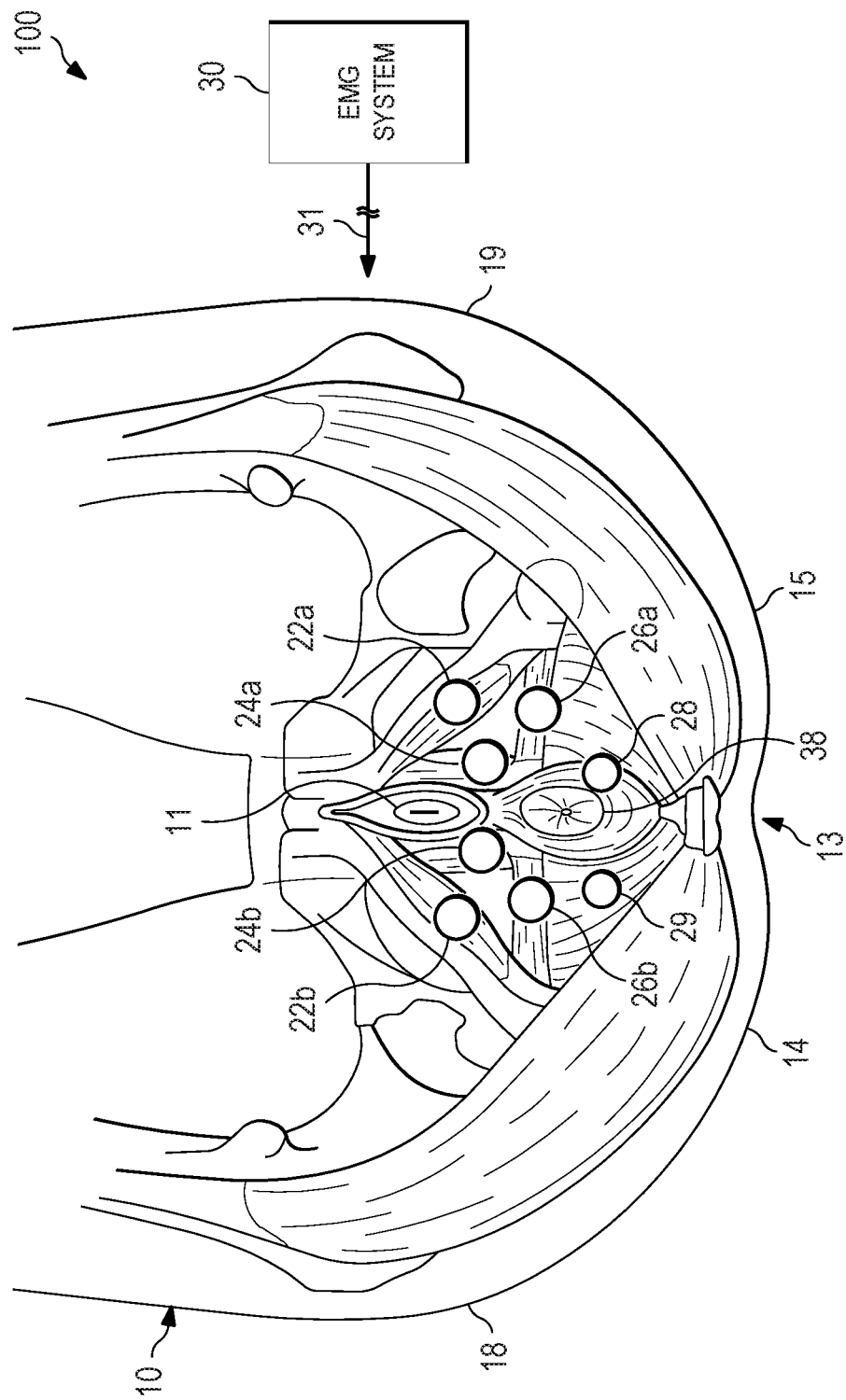
FIG. 1 is a partial cross sectional perspective bottom view of a labor monitoring system applied to a patient with stylized depiction of the patient anatomy.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

The present disclosure is directed to systems, devices, and methods for monitoring and managing child birthing labor along with supporting or treating perivaginal tissue of a patient, e.g. pelvic floor muscles and tissues. In this disclosure, reference may be made interchangeably between "perivaginal tissue" and "pelvic floor." "Perivaginal tissue" as used herein may refer to those muscles, skin, soft tissue, and nerves at, surrounding, adjacent, or near the vaginal opening or anus of a patient. Thus, "perivaginal tissue" refers to muscles that are associated with the "pelvic floor." These systems introduce novel elements and methods that may improve the reliability, the predictability, and the effectiveness of labor along with supporting or treating the perivaginal tissues. Various embodiments provide feedback to medical staff and patients regarding pelvic floor muscle activity and, in some embodiments, pressure levels, due to physiological transformations such as those that occur during muscle contractions (involuntary and/or voluntary) during child delivery, or device application. Electrical sensors (e.g., electrodes) are placed non-invasively adjacent various muscles of the pelvic floor during labor in order to monitor activity of these muscles as they are engaged during pushing. In an embodiment, these electrodes may be electromyography (EMG) sensors. Monitoring the activity of one or more muscles of the pelvic floor may provide a subjective measurement and indication of effective pushing, which medical staff and/or the patient being monitored may use to modify voluntary pushing efforts. For example, monitoring the pelvic floor muscles may provide useful information regarding rotation and flexion of the fetal head in passing through the birth canal. The electrical sensor monitoring may also be used to noninvasively obtain uterine measurements from the data collected from the pelvic floor and/or anal sphincter regions. Monitoring of voluntary pushing via electrical sensors (such as EMG sensors) placed non-invasively at the pelvic floor may also aid in determining whether a Cesarean section is likely necessary or not, e.g. by identifying potentially stalled labor.

Further, in embodiments of the present disclosure perivaginal tissue may also be supported during monitoring of the pelvic floor. Supporting the perivaginal tissue of a patient during $2^{nd}$ stage labor may reduce the incidence of a number of complications and conditions, including, for example, pelvic floor incontinence or dysfunction (overstretching of pelvic floor muscles, ligaments, nerves, and tendons), organ prolapse resulting from the over stretching, incontinence secondary to pressure and stretching exerted on bladder and bladder neck, over stretching due to use of forceps in delivery, perineum tears and lacerations due to over stretching, forceps use, or uncontrolled flexion/extension of the fetal head as it descends, and hemorrhoids. In embodiments where a perivaginal support device is applied at the same time as the electrodes, application of pressure in the perivaginal region can be sensed as a tactile sensation by a patient, often even after administration of an epidural. This may provide a pushing focal point to enhance the effectiveness of contractions and voluntary pushing. This may result in a shortening of second stage labor by enhancing the effectiveness of contractions and pushing in advancing the baby down the birth canal. This may reduce the necessity of Cesarean section deliveries by encouraging more effective pushing via electrode or electrode/pressure feedback and also informing medical staff regarding the likelihood of successful vaginal birth. The perivaginal support device may also cover all or most of the anal orifice and thereby suppress defecation, hemorrhoid development, and/or advancement of existing hemorrhoids.

In embodiments where a perivaginal support device is used, the perivaginal support device may include pressure detecting and monitoring capabilities of varying degrees. These varying degrees may include detecting and monitoring pressure ranges that provide therapeutic support and push feedback, detecting and monitoring pressure ranges indicative of increases in pressure level above the static pressure that provide feedback on push effectiveness, and detecting and monitoring pressure ranges above desired pressures and may warrant adjusting the perivaginal support device in order to alleviate some the pressure on the patient, in embodiments where the perivaginal support device is used.

FIG. 1 illustrates a partial cross sectional perspective bottom view of a labor monitoring and support system 100 applied to a patient 10. In FIG. 1, the patient 10 is shown in partial cross section to illustrate a portion of various muscles of the pelvic floor and one or more electrodes placed over some of those muscles. According to aspects of the present disclosure, the electrodes may be EMG sensors. EMG is used as one example of a system that can detect electrical signals from one or more muscles. As will be recognized, the present disclosure may utilize other types of detected electrical signals (and corresponding systems) without departing from the scope of the present disclosure. For simplicity of discussion, the present disclosure with be described with respect to EMG systems and devices. The patient 10's buttocks 14 and 15 are also shown. The respective crowns of the buttocks 14 and 15 are laterally adjacent the pelvic floor region. The gluteal cleft 13 is between buttocks 14 and 15. The buttocks 14 and 15 extend laterally toward lateral flanks 18 and 19, respectively. The crowns of each buttocks 14 and 15 in essence define the midline of each leg and the lateral flanks 18 and 19 are the area lateral of the leg/buttocks midline. The lateral flanks 18 and 19 may include, for example but without limitation, all or a portion of the lateral buttocks, hips, or upper thigh of the patient 10.

The EMG sensors placed over some of the pelvic floor muscles includes EMG sensors 22a and 22b placed over the bulbocaervnosus muscles, EMG sensors 24a and 24b placed over the ischiocavernosus muscles near the vaginal opening 11, EMG sensors 26a and 26b placed over the transverse perineal muscles, at least one EMG sensor 28 placed over the external anal sphincter muscle near the anal orifice 38, and at least one EMG sensor 29 placed over the levator ani muscle in at least one location. These EMG sensors are shown for purposes of illustration only. As will be recognized, more or fewer sensors than those shown in FIG. 1 may be placed to monitor various muscle activity of the pelvic floor. In an embodiment, the EMG sensors placed over these muscles are surface electrodes that are placed, e.g., on the skin surface over or near the indicated muscles in the regions shown. In an alternative embodiment, the EMG sensors may be needle electrodes inserted through the skin at locations of the pelvic floor.

The labor monitoring and support system 100 also includes an EMG system 30. The various EMG sensors 22a-22b, 24a-24b, 26a-26b, 28, and 29 are connected to the EMG system 30 via either wired coupler 31 or wireless connections (not shown in FIG. 1). In an embodiment, the EMG sensors may provide the data they measure as raw EMG signals to the EMG system 30. The EMG system 30 may receive the signals generated from the EMG sensors applied to the patient 10 and process them, for example to extract information regarding contraction and resting states of the muscles monitored at the pelvic floor. The EMG system 30 may convert raw EMG signals to root mean square (RMS) signals that may be used to measure activation timing for monitored muscles and/or an amount of force a monitored muscle generates. The EMG system 30 may convert the raw EMG signals, which may be in the time domain by default, into frequency domain signals in order to ascertain other aspects of the muscles, such as muscle fatigue and different activity from different types of muscle fibers.

In use, medical staff may use the labor monitoring and support system 100 while the patient 10 is in labor, such as during the second stage of labor where a child is entering the birthing canal of the patient 10. For example, prior to or during the second stage of labor, medical staff may prepare the skin at the areas where the EMG sensors 22a-22b, 24a-24b, 26a-26b, 28, and 29, or some subset thereof (or more than those shown), are placed. The EMG sensors 22a-22b, 24a-24b, 26a-26b, 28, and 29 may then be placed, such as by applying a material to the skin or to a bottom surface of each EMG sensor in order to enable adherence between the EMG sensors and the patient 10's skin (in embodiments where surface electrodes are used). Further, the EMG sensors may be placed as "dry electrodes" or a gel placed between the electrodes of the EMG sensors and the patient 10's skin. At the time the EMG sensors 22a-22b, 24a-24b, 26a-26b, 28, and 29 are placed on the patient 10, medical staff may additionally perform tests to confirm that the EMG sensors 22a-22b, 24a-24b, 26a-26b, 28, and 29 have been properly placed, e.g. at the particular muscle's mid-line.

After the EMG sensors 22a-22b, 24a-24b, 26a-26b, 28, and 29 have been properly placed and are detecting signals from the underlying muscle(s), the EMG sensors 22a-22b, 24a-24b, 26a-26b, 28, and 29 may transmit their measurements as EMG signals via coupler 31 to the EMG system 30 for processing, analysis, and/or presentation. As part of the processing, analysis, and/or presentation, the EMG system 30 may use the data from the EMG signals to determine whether the patient 10's voluntary pushing efforts are effective or not. In an embodiment, this involves comparison of the collected EMG signals to a library of different possible patterns of pelvic floor muscle electrical activity, and use of the comparison to predict the efficacy of patient 10's voluntary pushing efforts. The EMG system 30 may also use this data to predict the success of labor (e.g., whether vaginal birth is likely to occur or not). Medical staff interacting with the EMG system 30 may view information processed from the EMG signals that is useful in suggesting more or less pushing, or in determining that a Cesarean section will or will not be necessary.

Figure 2:
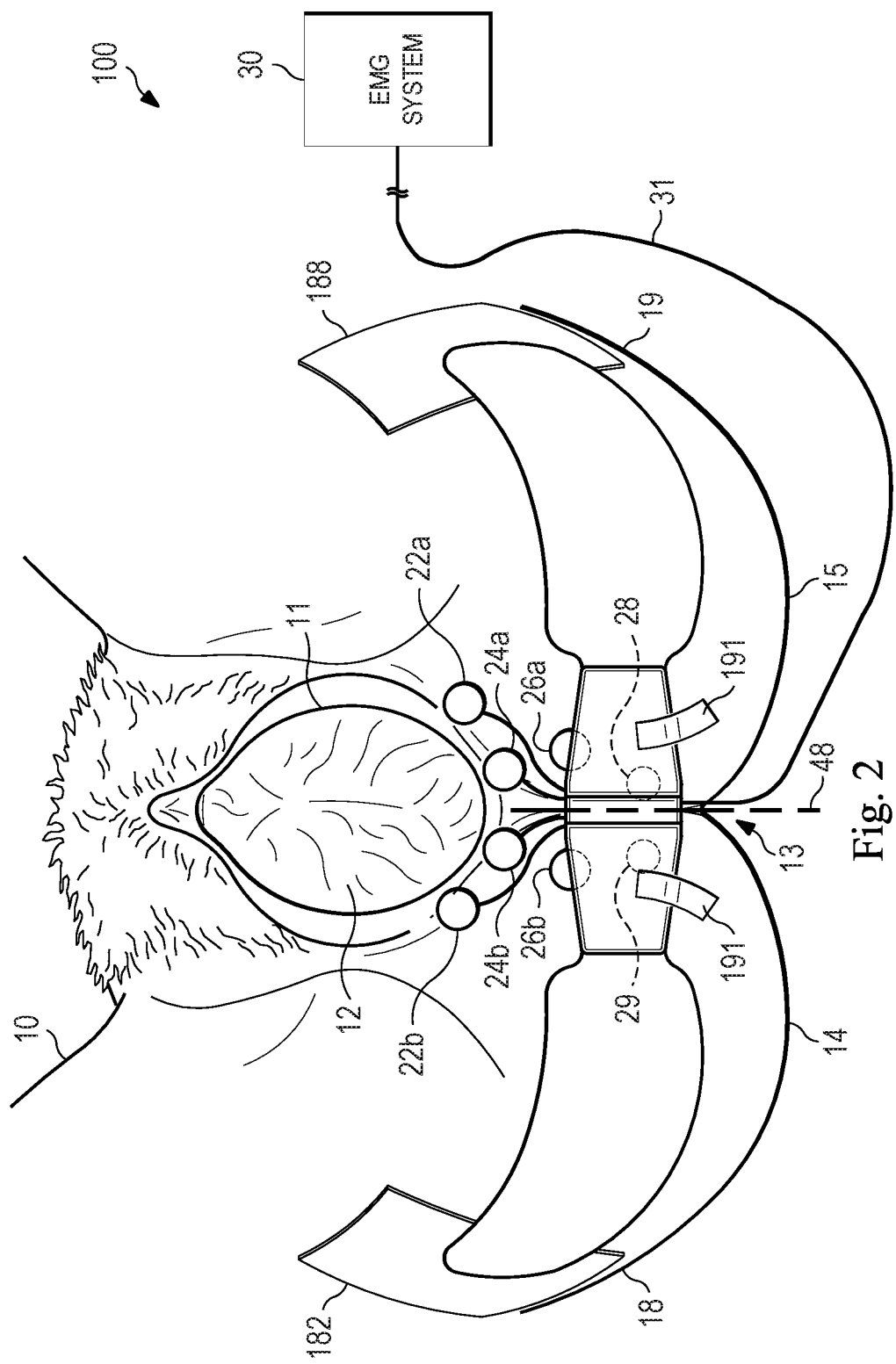
FIG. 2 is a partial perspective bottom view of a labor monitoring and support system applied to a patient during child delivery.

Turning now to FIG. 2, a labor monitoring and support system 100 according to an exemplary embodiment is illustrated in association with the perivaginal tissue of the patient 10. Specifically, FIG. 2 illustrates the patient 10 during a child birthing process.

The forces exerted during labor can be tremendous. For example, contractions during labor move a child 12 into the birth canal and ultimately, for a vaginal delivery, through the vaginal opening 11, as shown in FIG. 2. In an alternative birthing process, labor is commenced to move the child 12, but for a variety of reasons, the delivery does not occur vaginally. Instead, Caesarian delivery is performed through a surgical opening in the patient 10's abdomen. At least some of the pressure during childbirth is exerted against the tissues adjacent the anal orifice 38 in the pelvic floor area shown in FIG. 1. The result of these forces is that blood vessels near the anus, such as those in the external venous plexus, may bulge or rupture causing hemorrhoids or increasing their severity. Still further, other tissues and muscles in the pelvic floor region adjacent the anus may distend outwardly, causing lacerations such as tearing around the vaginal opening 11 or fissures from the anus. In addition to blood loss, pain, and discomfort, these lacerations can be a location for infections in the patient 10.

In embodiments of the present disclosure, a perivaginal support device may be used in cooperation with EMG sensors to monitor and support the perivaginal tissue of the pelvic floor region. In various embodiments, elements of the exemplary monitoring and support system 100 are shaped and structured to not only monitor and support perivaginal tissues during the birthing process without interfering with the birthing canal or vaginal opening 11, but also include features, elements, or structure that simplify application to the patient by providing indicators that detect pressure or indicate when desired application pressures are achieved. Some exemplary embodiments provide feedback to medical staff and patients regarding pressure levels due to device application or physiological transformations such as those that occur during muscle contractions during child delivery (e.g., where the perivaginal support device has a surface that is in contact with tissue of the patient's perivaginal region of the pelvic floor and a pressure sensor on the perivaginal support device detects an amount of pressure exerted against the device by the flexing). Additional exemplary embodiments provide user adjustment systems and techniques, allowing a patient as well as medical staff to adjust the devices for comfort and effectiveness. Examples of supporting devices are shown in U.S. Pat. No. 8,684,594, which is hereby incorporated by reference in its entirety. In this manner, the perivaginal tissue may be supported to inhibit damage to the tissue near the anal orifice 38, both internally and externally, to inhibit, for example but without limitation, the formation or advancement of external hemorrhoids, and/or to inhibit the formation or advancement of lacerations of the perivaginal tissues.

Figure 3A:
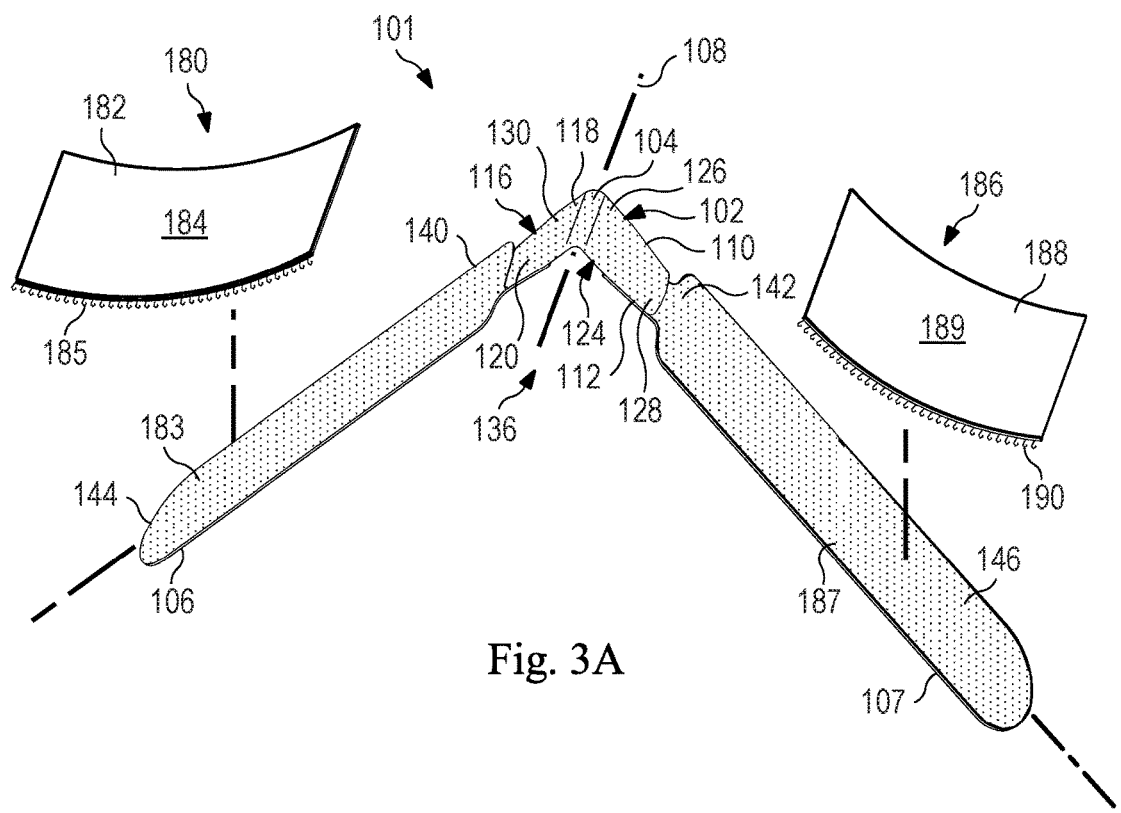
FIG. 3A is a perspective view of one aspect of a support system according to an exemplary embodiment.

FIG. 3A shows the perivaginal support device 101 in particular independent of the patient 10. The perivaginal support device 101 includes a perivaginal support member 102 having an external pressure surface 104 (also referred to as a contact surface) and a pair of extending securing members 106, 107 attached to and configured to assist in holding the perivaginal support member 102 in pressurized engagement with the perivaginal tissue (e.g., skin adjacent pelvic floor muscles and other tissue in the pelvic floor region of the patient 10) shown in FIGS. 1 and 2. The external pressure surface 104 extends along midline axis 108 between a posterior edge 110 and the anterior edge 112 of the perivaginal support member 102.

The perivaginal support member 102 includes a pair of compression elements 116, 124 formed as flanges. The first compression element 116 has a distal end portion 118 adjacent the pressure surface 104 and an opposing proximal end portion 120. The opposing second compression element 124 has a distal end portion 126 adjacent the pressure surface 104 and an opposing proximal end portion 128. The perivaginal support member 102 includes an outer surface 130 and an opposing inner surface 132 defining an access cavity 136.

As shown in FIG. 3A, the securing member 106 is attached to the first compression element 116 adjacent its proximal end portion 120. In a similar manner, the second securing member 107 is attached to the second compression member 118 adjacent its proximal end portion 128. In the illustrated embodiment, the securing members 106, 107 are elongated, flexible strips of a material. Midline end portions 140, 142 of the securing members 106, 107 attach to the compression elements 116, 118 of the perivaginal support member 102 while opposing lateral ends 144, 146 extend outwardly laterally from the midline or contact axis 108 of the perivaginal support device 101.

The first securing member 106 forms all or a part of a securing mechanism 180. In the embodiment in FIG. 3, the securing mechanism 180 includes the securing member 106 and an associated anchor pad 182. In this example, the securing member 106 includes a first half of a releasable fastening system on a surface 183, such as a hook and loop system or a releasable adhesive system. In the illustrated embodiment, the anchor pad 182 has a generally square shape that is shorter in length and wider than elongated securing member 106. The shape of the anchor pad is shown for illustration purposes and may take any form that is suitable for fixing to a patient or inanimate object, as well as joining to the elongated fixation member. The anchor pad 182 includes a first surface 184 having an adhesive surface adapted for joining to the patient's skin or some inanimate object. The opposing surface 185 includes the second half of the releasable fastening system. In a similar manner, the securing member 107 forms all or part of a securing mechanism 186 and includes a releasable fastening system on surface 187, such as a hook and loop system or a releasable adhesive system. In this example, a second component of the securing mechanism 186 includes an anchor pad 188. In the illustrated embodiment, anchor pad 188 has a generally rectangular shape that is shorter in length and wider than elongated fixation member 107. The anchor pad 188 includes a first surface 189 having an adhesive surface adapted for joining to the patient's skin or some inanimate object. The opposing surface 190 includes the second half of the releasable fastening system.

In some embodiments, instead of using the hook and loop fastener arrangement discussed above, at least a portion of a surfaces 183, 187 of the securing members 106, 107 has an adhesive coating adapted for joining to a fixed object. The securing member 106 may be fixed to the inner surface 132 of the compression element 116. Likewise, the securing member 107 is joined to the proximal end portion 128 of the second compression element 124. At least a portion of a surface of the securing member includes an adhesive coating that can fix the securing member to another object. In one embodiment, the adhesive coating is adapted for releasably adhering to a patient's skin. In another embodiment, the adhesive is adapted for joining to an inanimate object or to itself. In this manner, the securing member can fix the position of the perivaginal support member 102 relative to the operating table or other fixture near the patient. In some embodiments, the securing members are formed of flexible tape. Further, while they have been described separately, in one embodiment, the securing members are formed by a continuous piece of material joined in the middle to the perivaginal support member 102.

FIG. 2 shows exemplary flip preventer straps 191 that may extend from sides at least partially in the direction of the axis 48 to reduce the likelihood that the perivaginal support member 102 will flip when under loading, during adjustment, or during patient movement. In some embodiments, the flip preventer straps 191 are formed of flexible surgical tape. In other embodiments, the flip preventer straps 191 are hook and loop fastener portions that attach to anchor pads similar to the anchor pads 188, but much smaller to comfortably adhere to the body.

In one embodiment, the perivaginal support device 101 is formed of biocompatible material suitable for contact with human tissue. Moreover, in one embodiment, the device is provided sterile in a package for single use application on a patient, although reusable devices according to the present teachings are also disclosed in the present description. In the single use type of embodiment, the device is cost effectively manufactured such that it is discarded after use. For example, the device 101 is formed by of a substantially rigid polycarbonate material. In one aspect, the device 101 is injection molded to substantially its final V-shaped form. The compliant pad is then applied to the apex and securing members are joined to the compression members via an adhesive. It is contemplated that securing members 106, 107 may be riveted, snapped or otherwise fixedly attached to the compression elements. Still further, in a different embodiment, the securing members are passed through a channel or other opening associated with the compression elements to loosely and/or removably join the securing member to the perivaginal support member 102. In one aspect, compression elements comprise a loop portion of a hook and loop fastening system, such as sold under the tradename VELCRO.

It is contemplated that in other embodiments, the perivaginal support member 102 is formed by compression molding, transfer molding, reactive injection molding, extrusion, blow molding, casting, heat-forming, machining, deforming a sheet, bonding, joining or combinations thereof. In other embodiments, suitable materials for device 101 include polymers, metals, ceramics or combinations thereof. The materials can be or include alone or in combination: hard solids, soft solids, tacky solids, viscous fluid, porous material, woven fabric, braided constructions, or non-woven mesh. Examples of polymers include polyethylene, polyester, Nylon, Teflon, polyproplylene, polycarbonate, acrylic, PVC, styrene, PEEK, etc. Examples of ceramics include alumina, zirconia, carbon, carbon fibers, graphites, etc. Examples of suitable metals include titanium, stainless steel, cobalt-chrome, etc.

It is contemplated that in still further embodiments, the compliant pad can be made from or includes at least one of the following, either alone or in combination: woven fabric, non-woven mesh, foam, film, porous sheet, and non-porous sheet. At least the perivaginal support member 102 and compliant pad are sterilized by known techniques; such as ethylene oxide gas, gas plasma, electron-beam radiation or gamma radiation. Such materials are available from various suppliers such as 3M. In a similar manner, the fixation members or straps may be formed of hook and loop fastening systems available from 3M. Adhesive fixation systems may be adhesive a Rayon woven tape on a liner (1538L from 3M). The tape may include liners to prevent premature tape adhesion. In one embodiment, the liners include a cut between the midline end adjacent perivaginal support device 101 and the lateral end.

Figure 3B:
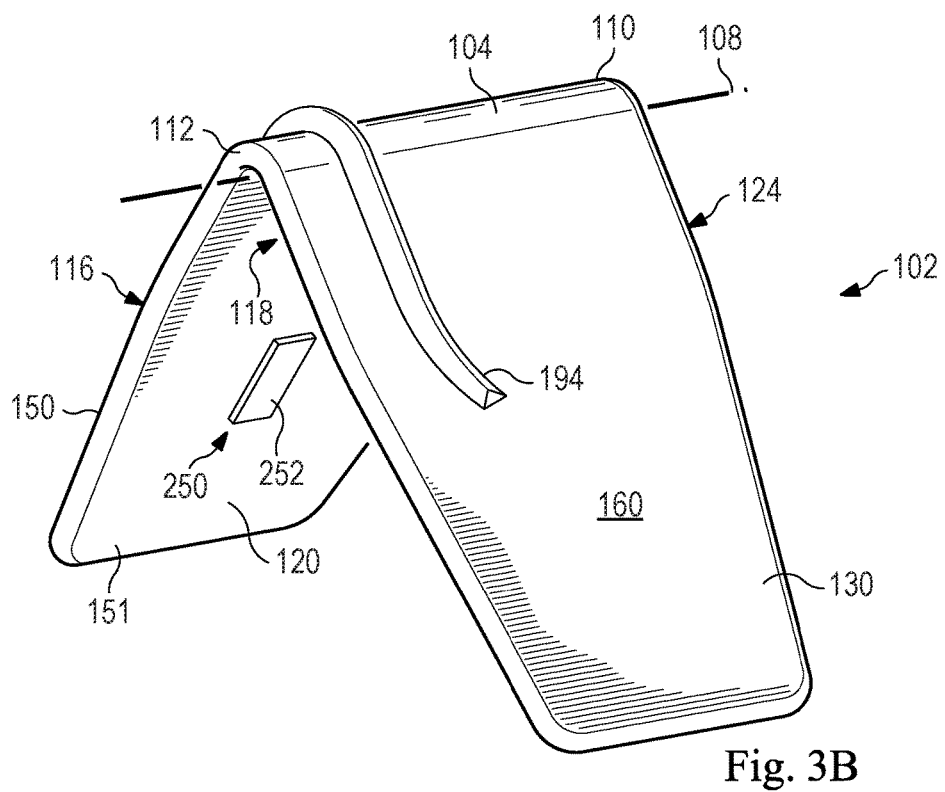
FIG. 3B is a perspective view of a portion of the support system according to an exemplary embodiment.
Figure 5B:
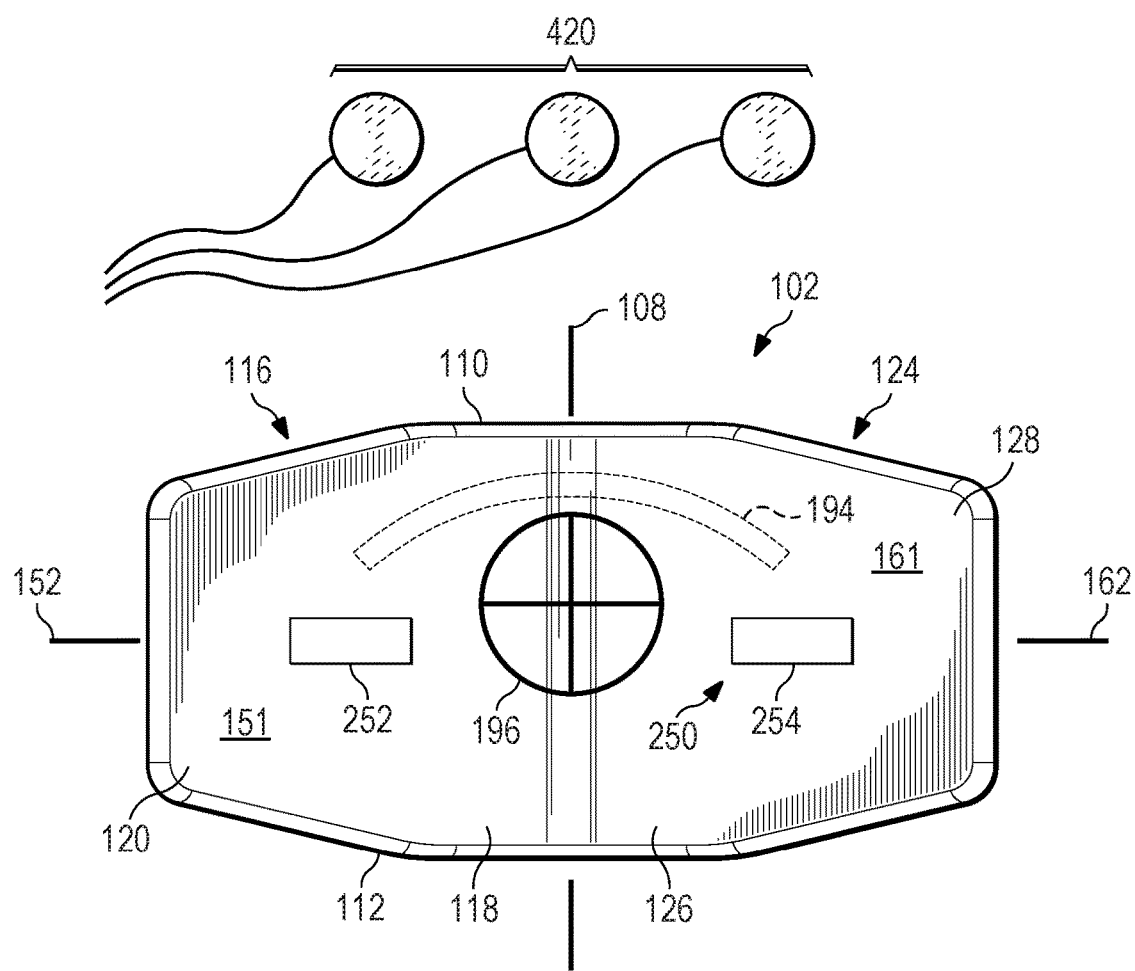
FIG. 5B is an end view of a portion of the labor monitoring and support system of FIG. 5A.

The exemplary perivaginal support member 102 in FIG. 3A is shown in additional detail in FIG. 3B. In the example shown the first and second compression elements 116, 124 are integral with and define a portion of the perivaginal support member 102. The distal end portion 118 of the compression element 116 transitions into the pressure surface 104. The compression element 116 also includes an elongated, planar exterior side wall 150 extending from the distal end 118 to the proximal end 120. The compression member 116 extends generally along axis 152 (e.g., as shown in FIGS. 5B, 6B, 7B) which is substantially transverse to the midline axis 108. The compression element 116 extends at an oblique angle with respect to an axis that is normal to the pressure surface 104. It will be understood that this axis normal to the pressure surface 104 is also representative of the sagittal plane of the body and midline axis 108 extends generally within the sagittal plane. In a similar manner, the distal end 126 (FIG. 3A) of the compression element 124 transitions into the pressure surface 104. The compression element 124 also includes an elongated, planar exterior side wall 160 extending from the distal end 126 to the proximal end 128 (FIG. 3A). The compression element 124 extends generally along an axis 162 (e.g., as shown in FIG. 5B, 6B, or 7B) which is substantially transverse to the midline axis 108. The compression element 124 also extends at an oblique angle with respect to the axis normal to the pressure surface 104. It will be appreciated that in the illustrated embodiment, compression element 124 extends at an oblique angle substantially equal to the oblique angle at which compression element 116 extends. In some embodiments, the oblique angles are each within the range of about 5 to 25 degrees. In other embodiments, the oblique angles are each within the range of about 10 to 20 degrees, and in yet other embodiments, are with a range of about 15 to 20 degrees.

The perivaginal support member 102 of the perivaginal support device 101 has an internal contact surface defined along the midline 108 opposing the external pressure surface 104. It will be understood that medical staff may apply pressure to this contact surface to move the perivaginal support member 102 into the operative position shown in FIG. 2 and/or apply additional pressure to compress at least some perivaginal tissue. The compression element 116 includes an interior wall 151 (e.g. as shown in FIG. 5B, 6B, or 7B) while the compression element 124 has an opposing interior wall 161 generally facing interior wall 151 (e.g. as shown in FIG. 5B, 6B, or 7B). The interior walls 151, 161, along with the internal contact surface define the access cavity 136 within the perivaginal support device 100. The configuration of the perivaginal support member 102 as described above results in a generally wedge shaped device. Still further, with the inclusion of the access cavity 136, the perivaginal support member 102 has a substantially V-shaped configuration with the pressure surface 104 defined at the apex of the V and the compression elements 116, 124 forming the legs of the V.

In some exemplary embodiments, the perivaginal support device 101 includes a pressure detecting system 250. The pressure detecting system 250 may be associated and configured with other components of the perivaginal support device 101, such as the perivaginal support member 102 or the securing members 106, 107. In some embodiments, the pressure detecting system 250 is integrally formed with components of the perivaginal support device 101 discussed above. That is, in some embodiments, the pressure detecting system 250 is a part of the perivaginal support device 101. In other embodiments, the pressure detecting system 250 is associated with the perivaginal support device 101 in a manner enabling the pressure detecting system 250 to monitor or detect the pressure on the perivaginal support device 101 (e.g., such as those that occur during muscle contractions during child delivery) or on the patient 10 (e.g., from an amount of tension applied with the securing members 106, 107). As will be recognized, the pressure detection system 250 (e.g. the strain gauges) may assume a variety of different shapes and sizes, be placed in a variety of different locations on the perivaginal support member 102 that do not interfere with EMG sensor operation (where applicable), and be secured to or with the perivaginal support member 102 in a variety of different ways without departing from the scope of the present disclosure.

The pressure detecting system 250 may be configured and arranged to detect changes in pressure, stress, or strain, either directly or indirectly, that may be indicative of the amount of pressure being applied on the perivaginal support device 101 or by the perivaginal support device 101 on perivaginal tissue of the patient 10. For example, the pressure detecting system 250 may directly measure pressure using pressure sensors, or may indirectly measure pressure by monitoring, detecting, or responding to changes in shape, structure, or arrangement of various components or elements making up the perivaginal support device 101. As will be discussed in more detail below, in various embodiments the pressure detecting system 250 may be used in cooperation with an EMG system 30 to provide additional detail regarding the progress and estimated efficacy of vaginal birth. In an embodiment, the EMG system 30 may receive data from the pressure detecting system 250 in addition to the data from EMG sensors. Alternatively, a separate monitoring system may receive and process the data from the pressure detecting system 250.

In exemplary embodiments, for example as shown in FIGS. 3B, 5B, and 7B, the pressure detecting system 250 comprises a plurality of strain gauges 252, 254 disposed on the perivaginal support member 102. A user interface, such as the one provided for the EMG system 30 as discussed with respect to FIG. 4 may be in communication with the strain gauges 252, 254. In some embodiments, the strain gauges 252, 254 form a part of the perivaginal support member 102, while in other embodiments, they are adhered to the perivaginal support member 102. In the examples shown, a first strain gauge 252 is attached to the first compression element 116 and a second strain gauge 254 is attached to the second compression element 124. The strain gauges 252, 254 are arranged to detect strain in the compression elements 116, 124 in a manner indicative of loading applied to the external pressure surface at the anterior end 112 of the perivaginal support member and of loading at the posterior end of the perivaginal support member 104 as applied by the securing members 106, 107. The strain gauges 252, 254 may be any type of strain gauge including for example, a mechanical strain gauge, an electrical resistance strain gauge, an optical strain gauge, or other type of strain gauge.

As already indicated, the strain gauges may communicate with a user interface that is configured to communicate information relating to the strain on the perivaginal support member 102 as detected by the strain gauges 252, 254, which is representative of pressure being applied by the perivaginal support member 102 to the patient 10. The user interface may display or otherwise convey to medical staff or the patient 10 detected changes in pressure level, may display or otherwise indicate whether the pressure is within a suitable range, or may display or otherwise provide other feedback to the health care provider or patient indicative of pressure during the child delivery process. In various embodiments, this display and/or other feedback may be provided together with, or separate from, data regarding the pelvic floor as interpreted from the EMG signals received. To provide this feedback regarding pressure specifically, the user interface may communicate with the strain gauges 252, 254. Depending on the embodiment, the user interface may communicate with the strain gauges 252, 254 either by wired connection or by a wireless connection.

In some embodiments, signals from the strain gauges are processed by a processing system, and the user interface may receive information from the processing system indicative of information obtained by the strain gauges. In some embodiments, the user interface is a table-top device separate from the EMG system 30 that may be viewed by medical staff or patient 10. In other embodiments, the user interface is a handheld structure, such a fob that may provide information to medical staff or patient 10. In other embodiments, the user interface may be integrated with the EMG system 30. Alternatively, a processing system may separately process data from the strain gauges 252, 254 and provide the results to the EMG system 30 for integration with and/or presentation with EMG data to medical staff or the patient 10. Depending on the embodiment, the user interface may communicate detected information in any manner that may be understood by medical staff or the patient 10. In one embodiment, the user interface displays values from the strain gauges indicative of strain. In simpler embodiments, the user interface may display a red light when the absence of strain indicates that the perivaginal support device 101 is not applying a desired pressure to the perivaginal support member 102 and a green light when the detected strain indicates that the perivaginal support device 101 is applying pressure within a desired range. Other interfaces are also contemplated. When the strain gauges 252, 254 are of the type measuring electrical resistance though a conductor, the user interface may also serve as a power source for the strain gauges. Other embodiments use strain gauges having an on-board power supply. Yet other arrangements are contemplated.

Some embodiments have a user interface in the form of a smartphone or tablet, or other similar device that is wired or wirelessly connected with sensors 252 and 254. In this embodiment, the user interface may operate a selectable application that may be downloaded to the user interface. In such embodiments, the patient 10 or medical staff may opt to view the information from the pressure detecting system on her own personal device. In some embodiments, the user interface may display a graph with a line tracing the detected pressure as a timeline, alone or in combination with one or more EMG readings or interpretations from the EMG system 30.

FIG. 3B also show a migration barrier 194 that extends at least partially along the exterior side wall 150 of the first compression element 116 and at least partially along the exterior sidewall 160 of the second compression element 124. In some embodiments, the migration barrier may be formed of a soft, flexible silicon material configured to prevent the migration of fecal matter that may be expelled during childbirth. In this embodiment, the perivaginal support member 102 may be located over the anus 38 and other muscles in the pelvic floor region so that the migration barrier 194 is disposed between the anus 38 and the vaginal opening 11. The migration barrier 192 may permit expelled matter to migrate only in the direction away from the vaginal opening 11. In the embodiment shown, the migration barrier 194 extends at an oblique angle relative to the axis 152, 162 (e.g., as shown in FIG. 5B) and may form a curved arc (e.g., as can be seen by the hidden lines in FIG. 5B). Other embodiments have a different angle and may be for example, purely linear or otherwise shaped.

Figure 4:
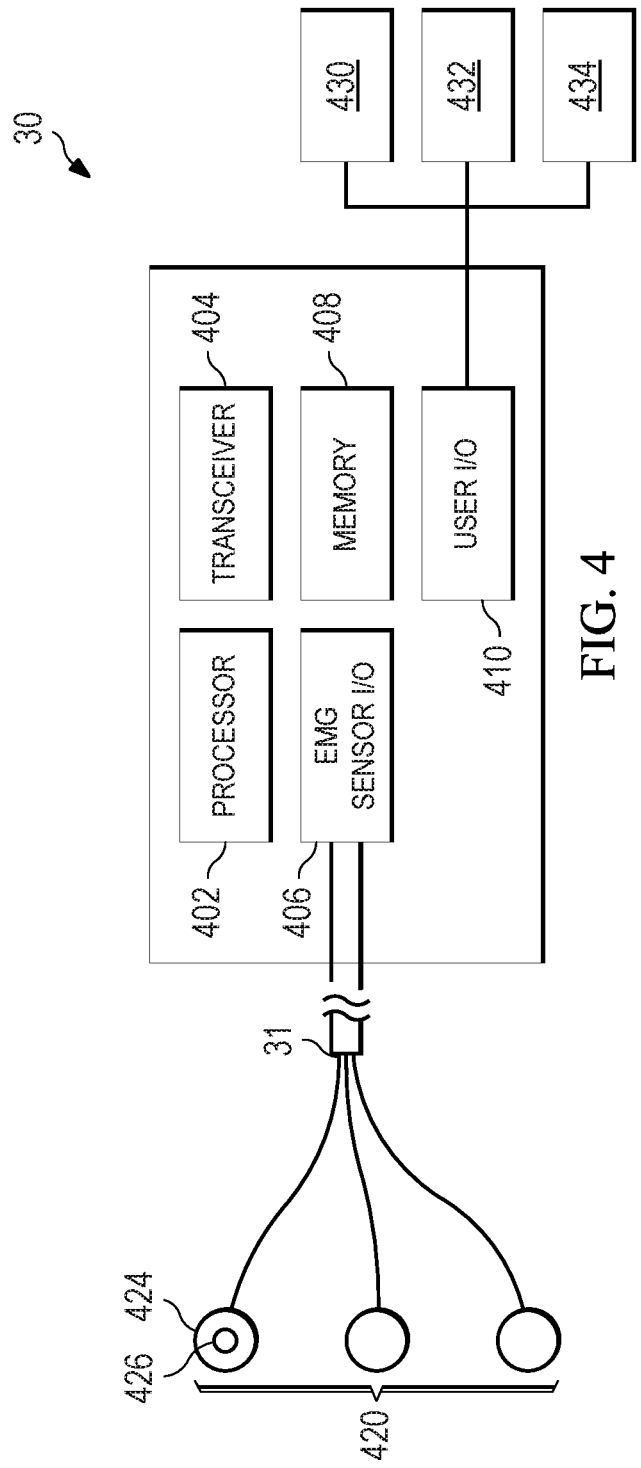
FIG. 4 is a block diagram of a labor monitoring system according to an exemplary embodiment.

FIG. 4 is a block diagram of a labor monitoring system 100 according to an exemplary embodiment. In an embodiment, FIG. 4 illustrates an example of the EMG system 30 of FIGS. 1 and 2. The EMG system 30 may include a processor 402, a transceiver 404, an EMG sensor input/output (I/O) 406, a memory 408, user I/O 410, display device 430, user I/O device 432, and physical I/O 434.

The processor 402 may be implemented using hardware or a combination of hardware and software. Although illustrated as a single processor, the processor 402 is not so limited and may comprise multiple processors. The processor 402 may include a central processing unit (CPU), a digital signal processor (DSP), an application-specific integrated circuit (ASIC), a controller, a field programmable gate array (FPGA) device, another hardware device, a firmware device, or any combination thereof. The processor 402 may also be implemented as a combination of computing devices, e.g., a combination of a DSP and a microprocessor, a plurality of microprocessors, one or more microprocessors in conjunction with a DSP core, or any other such configuration.

The transceiver 404 may include various components that enable the EMG system 30 to couple to a communication link (e.g., a wired or wireless communication link) for communication with other devices, systems, and/or networks. For example, the transceiver 404 may include a network interface card, for example including an Ethernet port (or multiple). The transceiver 404 may be bidirectional or unidirectional, depending on the embodiment. In embodiments where the EMG system 30 can communicate wirelessly with other devices, the transceiver 404 may include modem and radio frequency (RF) subsystems. The modem subsystem may be configured to modulate and/or demodulate data, such as after it has been processed by the processor 402. The RF subsystem may be configured to process (such as perform analog to digital/digital to analog conversion) modulated data either inbound to or outbound from the EMG system 30.

The EMG sensor I/O 406 may include hardware and/or software (e.g., firmware) that enables the EMG system 30 to interface with one or more EMG sensors 420. In embodiments where the EMG sensors 420 are wired sensors, the EMG sensor I/O 406 includes one or more ports and protocols that the wired distal ends of the EMG sensors 420 may connect with in order to convey their signals to the EMG system 30. In some embodiments, the EMG sensor I/O 406 may include the capability to convey signals to the EMG sensors 420, such as electrical pulses under the direction of the processor 402. The EMG sensor I/O 406 may be a single port configured to receive a bus of EMG sensor signals, or a plurality of ports, with a port for each EMG sensor 420 or some subset of EMG sensors. The EMG sensor I/O 406 may additionally include signal processing hardware/software to amplify, filter, convert, and/or otherwise process raw EMG signals from the EMG sensors 420 into a format that may be further manipulated according to aspects of the present disclosure. Alternatively, the EMG sensor I/O 406 may forward the raw data from the EMG sensors 420 to the processor 402 for performing one or more of these functions.

The memory 408 may include a flash memory, solid state memory device, hard disk drives, cache memory, random access memory (RAM), magnetoresistive RAM (MRAM), read-only memory (ROM), programmable read-only memory (PROM), erasable programmable read only memory (EPROM), electrically erasable programmable read only memory (EEPROM), other forms of volatile and non-volatile memory, or a combination of different types of memory. In an embodiment, the memory 408 includes a non-transitory computer-readable medium. The memory 408 may store instructions that, when executed by the processor 402, cause the processor 402 to perform operations described herein relating, for example, to processing EMG signals and/or pressure signals and outputting data for user viewing and interaction. Instructions may also be referred to as code, and should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The user I/O 410 may include hardware and/or software that enables the EMG system 30 to interface with input/output devices for the user, such as medical staff or the patient 10. The user I/O 410 may include the ability to support various ports and/or connectors, with accompanying protocols, to perform a multitude of functions. Some examples of ports include a universal serial bus (USB) port, a video graphics array (VGA) port, a digital visual interface (DVI) port, a serial port (e.g., RS-232), or high-definition multimedia interface (HDMI), to name just a few. Some examples of I/O devices include a display device 430, user I/O device 432, and physical I/O 434. The display device 430 may be a monitor, television, or other type of screen capable of displaying graphics and text data to a user. The user I/O device 432 may include a keyboard and/or a mouse, to name a few examples. In an embodiment, the display device 430 may have its own data input via a touchscreen capability. The physical I/O 434 may be, for example, a printer capable of printing data produced or relayed by the EMG system 30.

The transceiver 404 and one or more of the EMG sensor I/O 406 and the user I/O 410 may be, in alternative embodiments, integrated together (or some subset thereof, such as the EMG sensor I/O 406 and the user I/O 410).

The EMG system 30 includes one or more EMG sensors 420. The few shown in FIG. 4 are exemplary only, and in practice may include more or fewer sensors than those shown, as will be recognized by those skilled in the relevant art(s). Although shown with wired connections to the EMG system 30 (via the EMG sensor I/O 406), the EMG sensors 420 may alternatively be connected via a wireless connection, or some combination of wired and wireless connections (e.g., some EMG sensors are wired and some are wireless). The EMG sensors 420 may include surface electrodes, needle electrodes, or a combination of the types (e.g., some are surface electrodes and some are needle electrodes). The EMG sensors 420 may utilize dry or wet electrodes (when surface electrodes are used). The EMG sensors 420 may be single-use sensors that are discarded after every use, or sensors that may be sterilized and re-used. The EMG sensors 420 may be differential electrodes. EMG sensors 420 may also include a reference EMG sensor (not shown) that may be placed at a distance away from the other EMG sensors at the pelvic floor, for example at an electrically neutral area such as over a joint.

One of the EMG sensors 420 is further broken down in FIG. 4 to demonstrate some of the components of the EMG sensors 420. An EMG sensor 420 may include an electrode 426 and a surrounding contact pad 424. The electrode 426 may include an electrically conductive surface that may be relatively smooth or contoured for skin contact. In addition to the electrically conductive surface, the electrode 426 may include one or more hardware elements, e.g. one or multiple circuits integrated together or separate, to operate on signals detected from the monitored muscle. For example, the electrode 426 may include an amplifier to amplify detected signals, e.g. for transmission on a noisy wire to the EMG sensor I/O 406. In embodiments where the EMG sensors 420 are wirelessly connected to the EMG system 30, the electrode 426 may also include circuitry to transmit (and, in embodiments, receive) data to the EMG sensor I/O 406. Such circuitry may include, for example, an antenna and a controller (e.g., a processor) to format or condition the data and signal for wireless transmission. Various protocols may be used for data transmission, as will be recognized by those skilled in the relevant art(s). Further, the electrode 426 may represent a single electrode or multiple electrodes whose data may be treated separately or aggregated together to represent electrical activity of the underlying muscle. The electrode 426 may be an analog or a digital electrode. The contact pad 424 may be made of any suitable material for assisting in adhering to a patient's skin without interfering with signals at the electrode 426.

In operation, one or more of the EMG sensors 420, e.g. all those that have been placed over the same or different muscles of the pelvic floor area (such as those discussed above with respect to FIG. 1) detect electrical activity at the muscles and convey this activity as EMG signals to the EMG sensor I/O 406. The EMG sensor I/O 406, on its own or in cooperation with the processor 402, processes the signals received from the EMG sensors 420. In one form this involves converting raw EMG signals to RMS signals that may be used to measure activation timing for monitored muscles and/or an amount of force a monitored muscle generates. In another form this also, or alternatively, involves converting the raw EMG signals, which may be in the time domain by default, into frequency domain signals in order to ascertain other aspects of the muscles, such as muscle fatigue and different activity from different types of muscle fibers.

In one aspect, the processor 402 compares the processed EMG signals, the raw EMG signals, or some combination, to a library of different possible patterns of pelvic floor muscle electrical activity, and uses this to predict the efficacy of patient 10's voluntary pushing efforts. The library may be maintained in the memory 408 or be dynamically retrieved from a remote device or system via the transceiver 404. In addition or in the alternative, the processor 402 may compare the processed EMG signals to one or more predetermined thresholds. According to instructions kept in the memory 404, the processor 402 may additionally process the data by using the results of the comparison, as well as other processing on the data, to predict whether the patient 10's voluntary pushing efforts are effective or not. The EMG system 30 may additionally derive uterine measurements from the data obtained from one or more of the EMG sensors 420. The EMG system 30 may also use this data to predict the success of labor (e.g., whether vaginal birth is likely to occur or not).

In embodiments where the system 100 also includes pressure sensors, the data obtained from the pressure sensors may be received in a raw format, such as via the transceiver 404, and processed according to instructions in the memory 408 by the processor 402. Alternatively, the pressure data may have been processed previously by a separate processing device and transmitted, via wired or wireless connections, to the EMG system 30 via the transceiver 404 for further processing and integration with the data produced from the EMG sensors 420. Together, the EMG sensor data and the pressure data may provide a holistic view of the efficacy of pushing (as interpreted from the pelvic floor muscle data), whether the pressure is beyond an acceptable threshold level, or a given amount of pressure over a given threshold period of time, that may indicate a higher likelihood of damage to one or more muscles or nerves of the patient 10 or indicate stalled labor. In an alternative embodiment, the EMG system 30 may instead transmit its EMG data, via transceiver 404, to another processing system that may combine the EMG data with pressure data and/or other data to provide analysis and prediction.

Where the EMG system 30 performs the processing, analysis, and prediction, the EMG system 30 may output processed data, including results of analysis and prediction, to the display device 430. Medical staff and/or the patient 10 interacting with the EMG system 30 may view information processed from the EMG signals via the display device 430. The user may use the user I/O device 432 to further manipulate the data generated as viewed via the display device 430. In an embodiment, the user may use the data generated via the EMG system 30 assist in coaching the patient 10 to push more or less, and/or predict whether a Cesarean section may or may not be necessary.

Figure 5A:
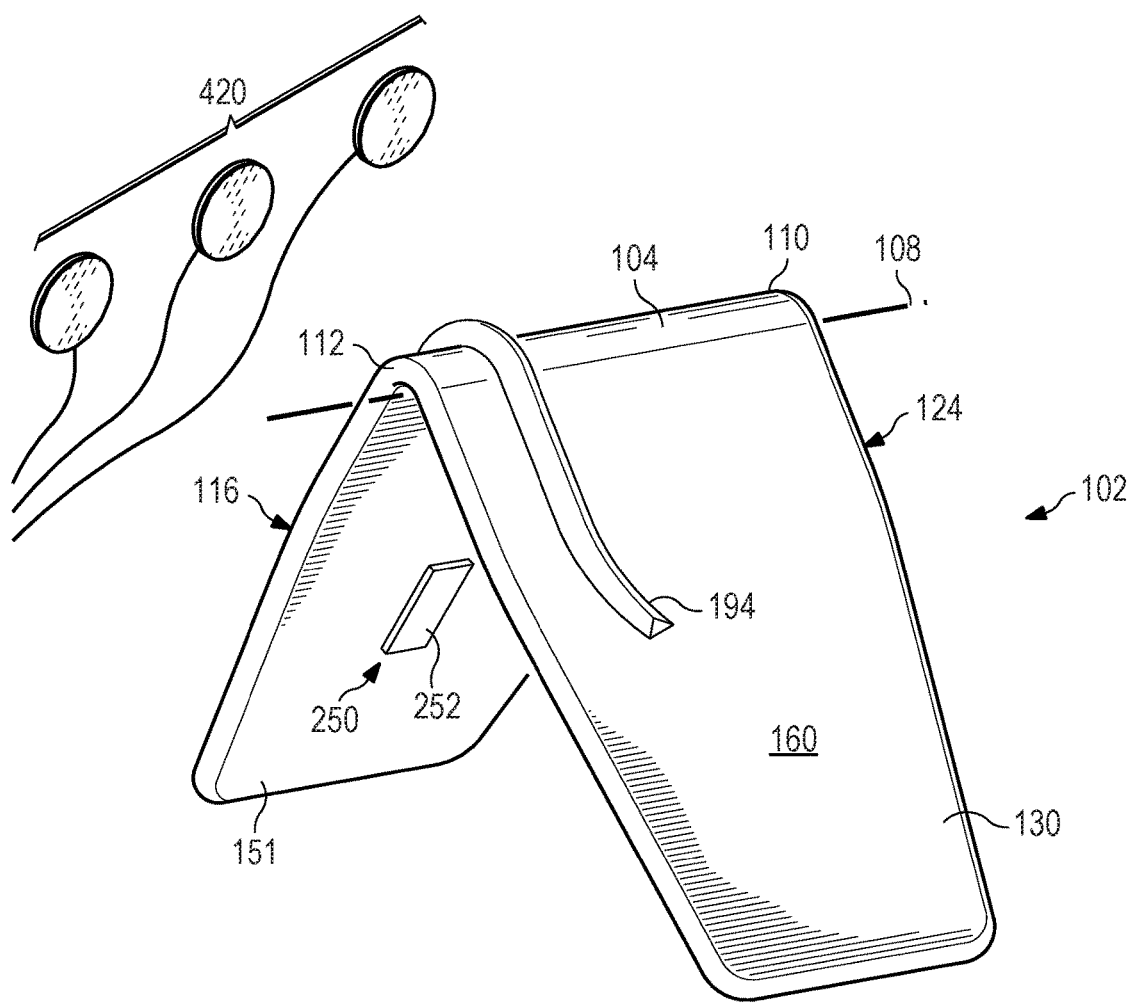
FIG. 5A is a perspective view of a portion of a labor monitoring and support system according to an exemplary embodiment.

FIG. 5A is a perspective view of a portion of the labor monitoring and support system 100 according to an exemplary embodiment. For purposes of simplicity of discussion, only those elements that differ from what was introduced above with respect to FIGS. 3A, 3B, and 4 will be addressed. In FIG. 5A, the EMG sensors 420 are separate from the perivaginal support device 101. Further, the perivaginal support device 101 includes pressure detection system 250 including strain gauges 252, 254. In an embodiment, the EMG sensors 420 are first placed over target perivaginal tissues in the pelvic floor region. The perivaginal support device 101 may then be positioned behind the EMG sensors 420.

FIG. 5B is an end view of a portion of the labor monitoring and support system 100 of FIG. 5A. FIG. 5B shows an indicium 196 that may assist medical staff to properly locate the perivaginal support member 102 on the patient 10. In this example, the indicium 196 is a target shape formed on the perivaginal support member 102. In use, the medical staff may align the target with a body reference marker, such as the anus 38. This may help ensure the perivaginal support member 102 is properly located to support or treat perivaginal tissue of the pelvic floor while maintaining suitable spacing from the vaginal opening 11. Although a target shape is shown, other embodiments have other shapes or indicia as indicators. Indicia may find particular utility when using a transparent perivaginal support member 102. In this example, the indicium 196 is spaced off-center from the axes 152, 162 in order to provide a suitable position of the perivaginal support member 102 on the patient.

Referring now to both FIGS. 5A and 5B, as well as FIGS. 1-2 and 3A, 3B, in an embodiment, medical staff may position the patient 10 to expose the perivaginal region of the patient 10. In the child birthing process, the patient 10 may be positioned in stirrups attached to a delivery table (not shown). The perivaginal device 101 is then moved adjacent the gluteal cleft 13 between buttocks 14 and 15. The perivaginal device 101 is positioned such that the midline 108 of the perivaginal support member 102 is substantially aligned with the patient 10's midline within the sagittal plane. The perivaginal support member 102 is advanced toward the anal orifice 38 (generally within the sagittal plane toward the head of the patient 10) to bring the pressure surface 104 into contact with the perivaginal tissues. Continued advancement of the perivaginal support member 102 toward the anal orifice 38 applies pressure through the pressure surface 104 to the perivaginal tissues, as well as to the EMG sensors 420 where they are between the perivaginal tissues and various surfaces of the perivaginal support member 102.

In one aspect, medical staff place at least one finger within the access cavity 136 and preferably against internal contact surface 170 to advance the device 101 against the anal orifice 38. Since the embodiment of FIG. 5A includes the pressure detections system 250, the medical staff utilizes the pressure feedback associated with the perivaginal support device 101 to sense that the initial placement exceeds a first pressure threshold. In one exemplary embodiment, the first pressure threshold is within a pressure range of about 0-770 mm of mercury. In one aspect, the initial positioning of the perivaginal support device 101 is spaced from or only in touching engagement without creating pressure when the patient 10 is not experiencing a contraction. As a contraction occurs or the patient 10 pushes, the perivaginal tissues will tend to protrude thereby engaging the perivaginal device 101 with a pressure that can be felt by the patient 10 through tactile feedback and sensed by the pressure detection system 250. In still a further aspect, the pressure thresholds needed for adequate tactile sensation vary between patients such that the first pressure threshold may be in a range from 40-120 mm of mercury. In a further form, the second pressure threshold needed to enhance tactile sensation need only to be higher than the first pressure. In one aspect, the second pressure threshold can be in the range of 80-250 mm of mercury.

With continued pressure applied by the medical staff to the access cavity 136, and/or internal contact surface 170, the elongate securing member 107 extends laterally of the anal orifice 38 away from the gluteal cleft 13 and is releasably attached to the patient 10 to at least the lateral flank 18. In a similar manner, with compressive force applied by the medical staff to the perivaginal support member 102, the elongate securing member 107 extends laterally of the anal orifice 38 out of the gluteal cleft 13 and is secured to the patient 10 adjacent lateral flank 19 to maintain the perivaginal support device 101 on the patient 10 in the static pressure therapeutic zone exceeding the first threshold. Thus, the securing members 106, 107 of the perivaginal support device 101 do not extend along the patient 10's midline in the gluteal cleft 13 with the potential for interference with the birthing process, but instead extend substantially laterally from the patient 10's midline out of the gluteal cleft 13 and are attached at the patient's lateral flanks 18 and 19.

The extent of tissue deformation surrounding the anal orifice 38 when perivaginal support device 101 is applied may be a function of the patient anatomy and of the amount of compressive force applied during application of the perivaginal support device 101. In one aspect, it is contemplated that pressure applied in the direction of the patient 10 moves the anal orifice 38 inwardly 1 cm to 3 cm. In one embodiment, the lateral ends 144, 146 of the securing members 106, 107 extend beyond line 178 generally in the patient 10's sagittal plane. The securing members 106, 107 exert tension forces generally in the direction the rest of the patient's body. This tension force is applied to compression elements 116, 124, which are substantially rigid members capable of transmitting compressive forces to the perivaginal support member 102. The tension force applied on the lateral flanks 18 and 19 of the patient 10 in the direction of the patient's body is converted to compressive forces toward the buttocks 14, 15. The compressive forces may be transmitted by substantially rigid compression elements 116, 124 and ultimately to the pressure surface 104 to apply support and/or pressure to the perivaginal tissues. It will be appreciated that the lateral components of compressive forces applied may help to maintain the position of the perivaginal support member 102 and the EMG sensors 420 in place between the perivaginal tissues and the perivaginal support member 102, as well as tending to maintain access cavity 136 in an open position. It will be understood that while compression elements 116, 124 are sufficiently rigid to transmit compressive force toward the pressure surface 104, in one embodiment they are flexible, at least laterally, to bow or bend in response to force applied to the securing members 106, 107.

It will be appreciated that with the illustrated embodiment, the medical staff may reposition the perivaginal support member 102 and adjust the compressive force applied through the securing members 106, 107 to the pressure surface 104 by releasing or adjusting the attachment between the securing members 106, 107 and the patient 10.

Additionally, in the illustrated embodiments, the perivaginal support member 102 of the support system 100 is sized and positioned with respect to the patient 10, and the EMG sensors 420 positioned at the patient 10's pelvic floor region to allow for the passage of a child 12 through the birthing canal during childbirth. It is contemplated that the perivaginal support member 102 may be placed to support more or less of the perineum between the anus 38 and vaginal opening 11 depending on the medical staff's judgment and the progress of the child birthing process. Still further, it is contemplated that an elongated anterior to posterior device may be positioned to support at least a portion of the perivaginal tissue during the labor process. It is anticipated that the supporting device will be repositioned posteriorly away from the vaginal opening 11 prior to delivery of the child through the vaginal opening 11.

After the EMG sensors 420 are applied and at least a subset of them held in place between the patient 10's skin and the perivaginal support device 101, aspects of the system may be used as discussed above (and further below) to monitor muscles of the pelvic floor, determine uterine contractions, detect pressure, advise the patient 10 to increase or decrease pushing efforts, and provide information to assist in predicting whether vaginal birth will be successful or not so as to decide whether a Cesarean section will be necessary instead.

With the labor monitoring and support system 100 in position, the medical staff is allowed to position one or both hands within the access cavity 136 extending into the gluteal cleft. In this manner, the hands may be below the lowest portion of the vaginal opening 11 as the head of the child 12 passes out of the vagina. Thus, the hand within the access cavity 136 may be positionable less than 1 cm from the mother's vaginal opening 11 or perineum so the medical staff may support the head of the child 12 as is it is being born. The position of the EMG sensors 420 (e.g., as illustrated in FIG. 1 or 2), and of second edge of the perivaginal support device 101, also allows access to the tissue immediately below the vaginal opening 11 in the event an obstetric maneuver, such as an episiotomy, manipulation of the fetus, etc., is necessary. Further, as discussed above, in one aspect the perivaginal support member 102 is quickly repositioned or removed by releasing at least one of the straps from the anchor pads, an obstetric maneuver is performed, the perivaginal support member 102 is repositioned in a supporting position adjacent the anus 38 and the anchoring straps are repositioned on the anchor pads. Further, the EMG sensors 420 may be removed at the same time or after the removal of the perivaginal support member 102 or left in place, depending upon the need and/or medical staff/patient 10 preferences. Therapeutic cooling may also be applied by attaching or securing a cooling applicator in place using the labor monitoring and support system 100.

Figure 6A:
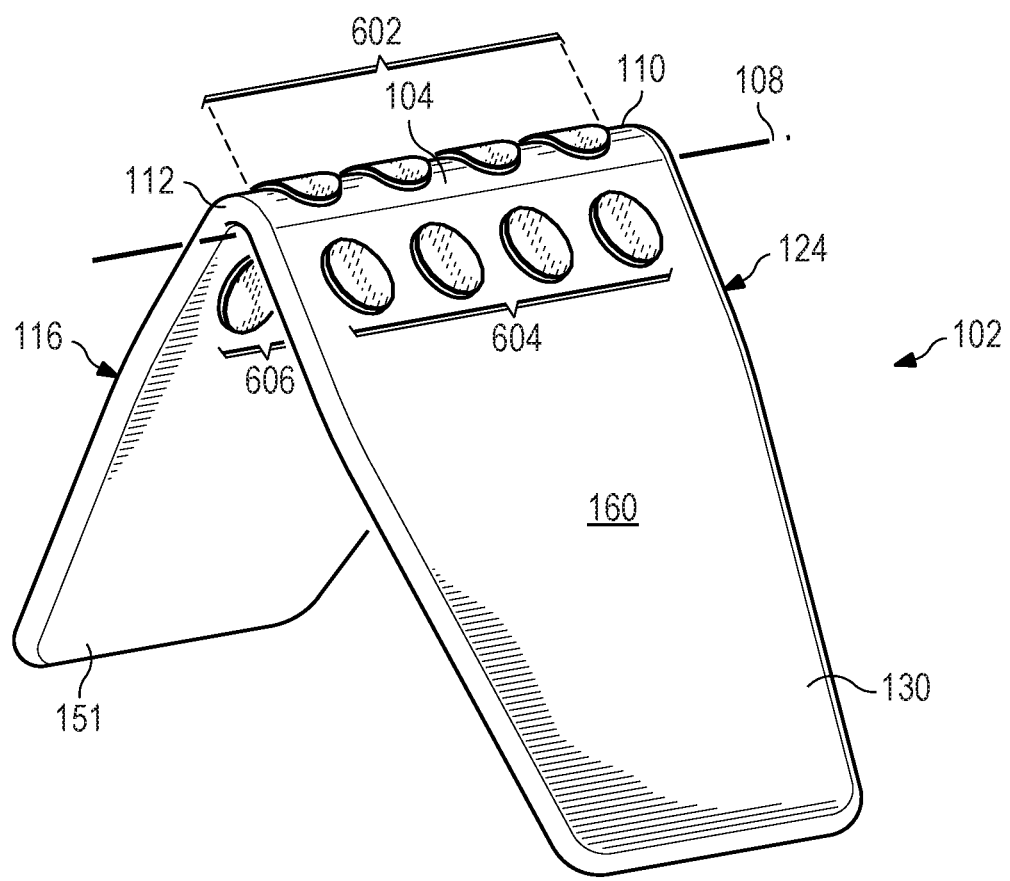
FIG. 6A is a perspective view of a portion of a labor monitoring and support system according to an exemplary embodiment.
Figure 6B:
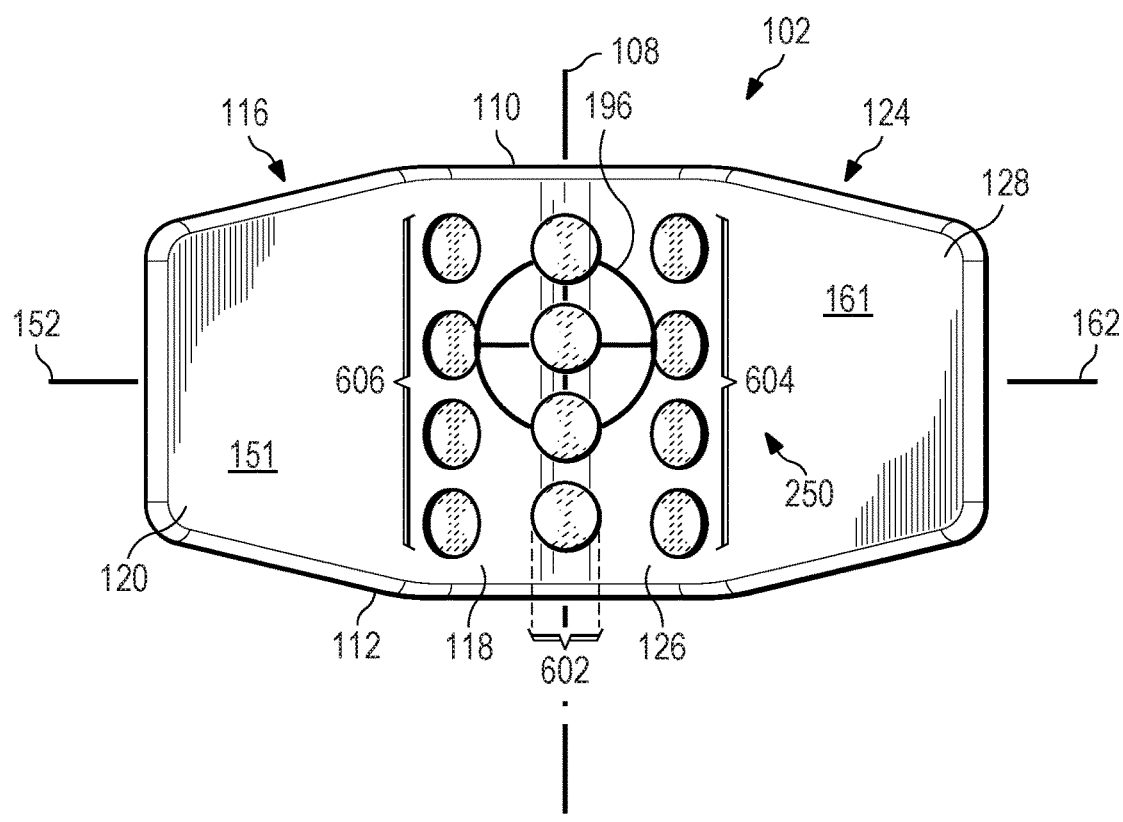
FIG. 6B is an end view of a portion of the labor monitoring and support system of FIG. 6A.

FIG. 6A is a perspective view of a portion of the labor monitoring and support system 100 according to an exemplary embodiment. For purposes of simplicity of discussion, only those elements that differ from what was introduced above with respect to FIGS. 3A, 3B, 4, 5A, and 5B will be addressed. FIG. 6B is an end view of a portion of the labor monitoring and support system 100 of FIG. 6A. The embodiments of FIGS. 6A and 6B do not include a pressure detection system.

In FIGS. 6A and 6B, EMG sensors are attached to or integrated with the perivaginal support device 101. EMG sensors are deployed in the embodiments of FIGS. 6A and 6B in arrays. This may include EMG sensor arrays 602, 604, and 606. The embodiments of FIGS. 6A and 6B illustrate three distinct arrays, though those skilled in the relevant at(s) will recognize that they may alternatively constitute one large array with multiple rows and columns spread across the device. Further or alternatively, it will be recognized that the number of EMG sensors in each array is exemplary— more or fewer EMG sensors in a given array may be deployed without departing from the scope of this disclosure. As shown, EMG sensor array 602 may be deployed at the external pressure surface 104 of the perivaginal support member 102. EMG sensor array 604 may be deployed at the planar exterior side wall 160, and EMG sensor array 606 at the planar exterior side wall 150, of the perivaginal support member 102. As a result, when the perivaginal support device 101 is put into place at the perivaginal area of a patient, one or more of the EMG sensors in the array 602 may be placed over one or more tissues of the pelvic floor along the sagittal plane between the anus 38 and vaginal opening 11 of the patient 10 for monitoring, and one or more of the EMG sensors in the arrays 604, 606 may be placed over one or more tissues of the pelvic floor adjacent to the sagittal plane, e.g. the levator ani and the transverse perineal, to name just a few examples.

In an embodiment, the EMG sensors of the arrays 602, 604, and 606 may be adhered to surfaces of the perivaginal support member 102, or alternatively integrated so that they form a part of the perivaginal support member 102. When integrated with the perivaginal support member 102, the EMG sensors 420 may be flush with, or still slightly elevated above, the surrounding surface of the perivaginal support member 102. In either embodiment, there is sufficient pressure from the placement and securing of the perivaginal support member 102 that at least some of the EMG sensors in the arrays 602, 604, and 606 will come into secure contact with the patient 10's skin over some tissue of interest.

With the perivaginal support device 101 with integrated EMG sensors applied, and at least a subset of the EMG sensors in place at the patient 10's skin at the pelvic floor, aspects of the system may be used as discussed above (and further below) to monitor muscles of the pelvic floor, determine uterine contractions, estimate pressure, advise the patient 10 to increase or decrease pushing efforts, and provide information to assist in predicting whether vaginal birth will be successful or not so as to decide whether a Cesarean section will be necessary instead.

Figure 7A:
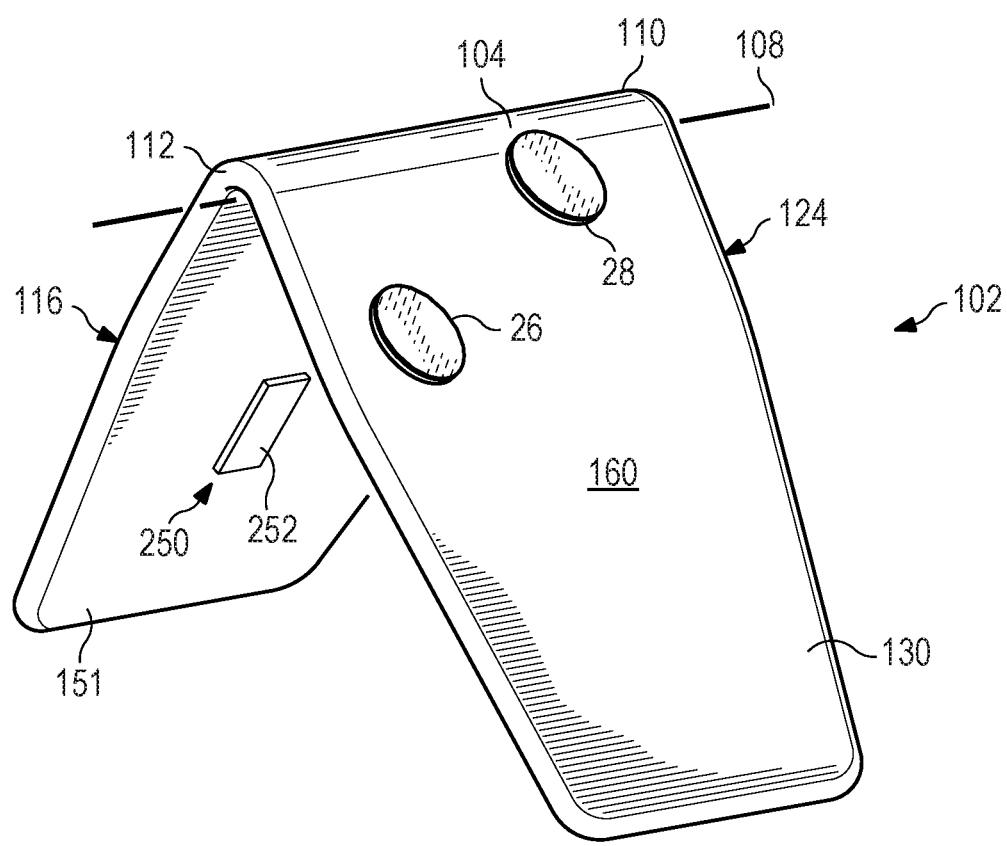
FIG. 7A is a perspective view of a portion of a labor monitoring and support system according to an exemplary embodiment.
Figure 7B:
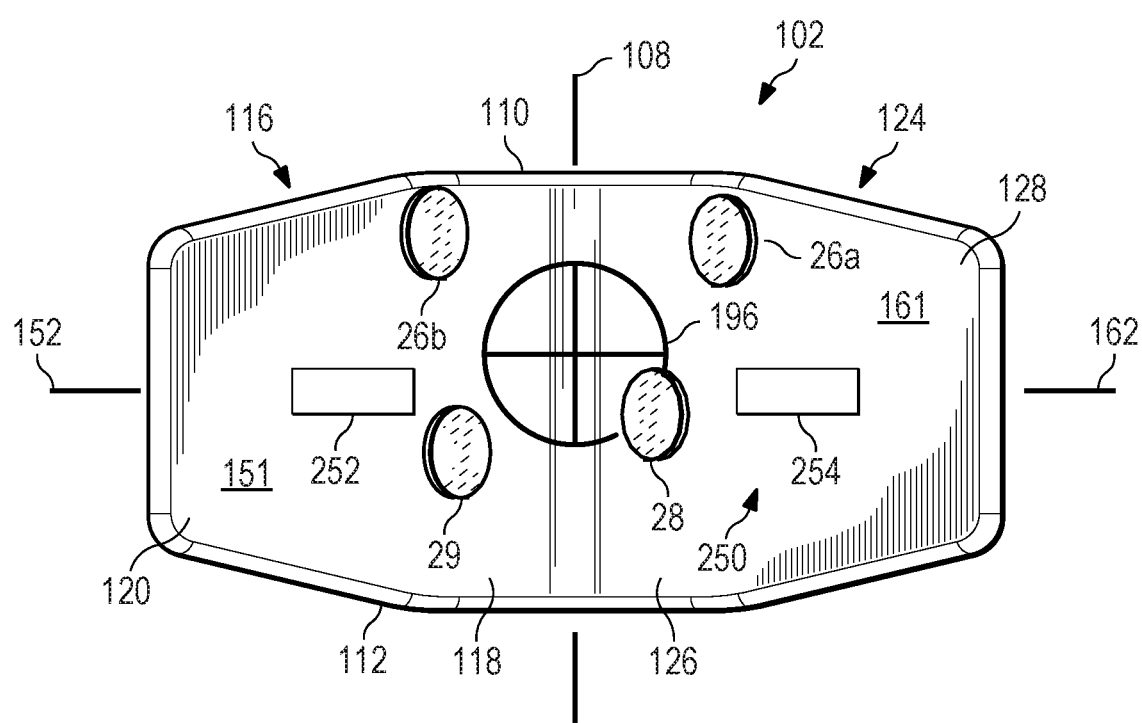
FIG. 7B is an end view of a portion of the labor monitoring and support system of FIG. 7A.

FIG. 7A is a perspective view of a portion of the labor monitoring and support system 100 according to an exemplary embodiment. For purposes of simplicity of discussion, only those elements that differ from what was introduced above with respect to FIGS. 3A, 3B, 4, 5A, 5B, 6A, and 6B will be addressed. FIG. 7B is an end view of a portion of the labor monitoring and support system 100 of FIG. 7A.

In FIGS. 7A and 7B, the EMG sensors are attached to or integrated with the perivaginal support device 101, similar to as discussed above with respect to FIGS. 6A and 6B. In contrast to the EMG sensor arrays of FIGS. 6A and 6B, the EMG sensors in FIGS. 7A and 7B may be integrated at locations more targeted to where specific muscle groups of the pelvic floor should be for exemplary patients 10. In the example of FIGS. 7A and 7B, EMG sensors 26a, 26b, 28, and 29 introduced in FIG. 1 are displayed. For example, sensors 26a and 26b are placed at locations of the perivaginal support device 101 that target the transverse perineal muscles, the sensor 28 is placed at a location that targets the external anal sphincter muscle, and the sensor 29 is placed at a location that targets the levator ani muscles. These placements are exemplary only, and those skilled in the relevant art(s) will recognize that the EMG sensors may be placed in other locations and/or more or fewer than those shown may be placed. Further or alternatively, it will be recognized that the number of EMG sensors attached to or integrated with the perivaginal support device 101 may be more or fewer than what is shown in FIGS. 7A and 7B without departing from the scope of the present disclosure.

In the embodiments of FIGS. 7A and 7B, the perivaginal support device 101 also includes pressure detection system 250 including strain gauges 525, 524, as discussed above with respect to FIGS. 5A and 5B. The EMG sensors and the pressure detection system may be placed in locations of the perivaginal support member 102 so that they do not interfere with the other's operations. When integrated with the perivaginal support member 102, the EMG sensors 26a, 26b, 28, and 29 may be flush with, or still slightly elevated above, the surrounding surface of the perivaginal support member 102. In either embodiment, there is sufficient pressure from the placement and securing of the perivaginal support member 102 that at least some of the EMG sensors will come into secure contact with the patient 10's skin over some tissue of interest, e.g. the muscle groups targeted by the locations of the EMG sensors at the perivaginal support member 102.

With the perivaginal support device 101 put into place, for example as discussed above with respect to FIGS. 5A and 5B, aspects of the system may be used as discussed above (and further below) to monitor muscles of the pelvic floor, determine uterine contractions, detect pressure, advise the patient 10 to increase or decrease pushing efforts, and provide information to assist in predicting whether vaginal birth will be successful or not so as to decide whether a Cesarean section will be necessary instead.

Figure 8:
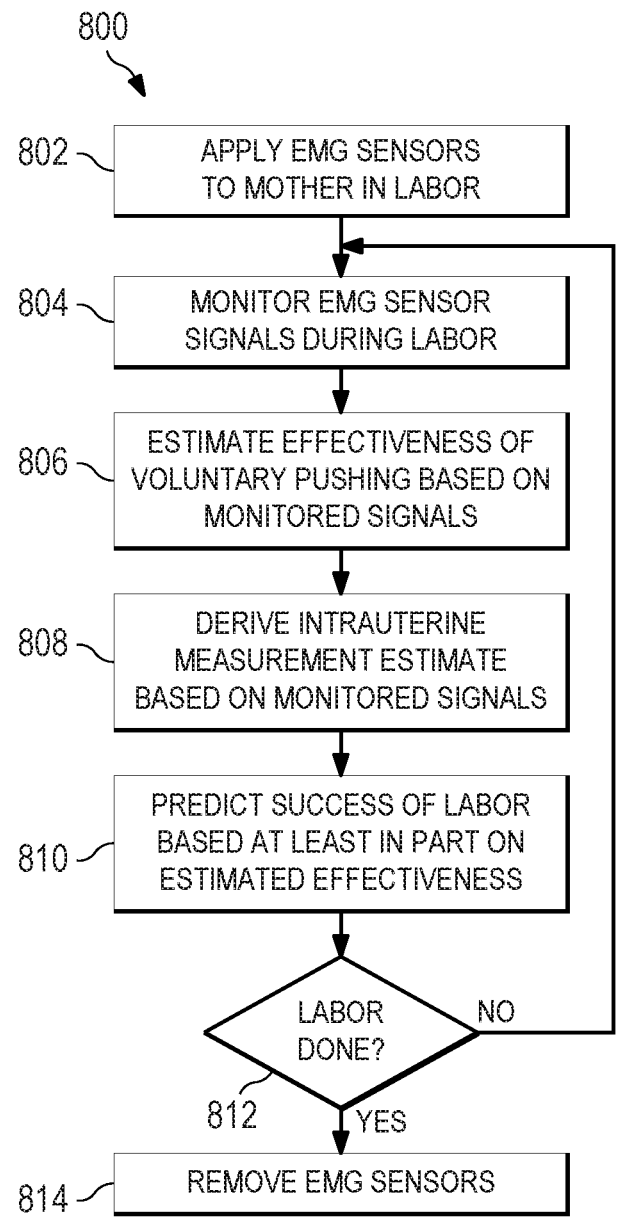
FIG. 8 illustrates a method of managing a mother's child birthing labor according to an exemplary embodiment.

FIG. 8 illustrates a method 800 of managing a mother's child birthing labor according to an exemplary embodiment. In an embodiment, the method 800 is an exemplary method with respect to the patient 10 discussed above with respect to FIGS. 1 and 2 specifically while using the EMG system 30 discussed with respect to FIG. 4.

At step 802, medical staff apply one or more EMG sensors 420 to a patient in labor, for example some time before or at the start of the second stage of labor. In an embodiment, the EMG sensors 420 are placed over some of the pelvic floor muscles including the bulbocaervnosus muscles, transverse perineal muscles, external anal sphincter muscle, and levator ani muscle to name a few examples. Prior to applying the one or more EMG sensors 420, the medical staff may first prepare the skin in the pelvic floor area by cleansing the area, removing any dead skin (e.g., by way of an abrasive paste or swab), applying alcohol swabs, and/or removal of any hair that may be in locations of desired monitoring.

At step 804, the EMG system 30 monitors signals produced and received from the EMG sensors 420 during labor. These signals may come in raw EMG formal. The EMG signals are processed at the EMG system 30 according to various aspects of the present disclosure, such as those discussed above. The EMG system 30 may receive the EMG signals from the EMG sensors 420 via wired and/or wireless signal paths, depending on the capabilities of the EMG system 30 and EMG sensors 420.

At step 806, the EMG system 30 estimates an effectiveness of voluntary pushing by the patient 10 based on the monitored and processed EMG signals received from the EMG sensors 420. The effectiveness of voluntary pushing may be estimated from the EMG signals based on a variety of factors, for example whether an amplitude of exertion of any one or more of the monitored pelvic floor muscles exceeds or falls below a predetermined threshold, whether an average value of some subset or all of the monitored pelvic floor muscles exceeds or falls below a predetermined threshold, or whether a signal profile of the EMG signals exhibits similarity to a stored profile in a library, e.g. exceeds a specified similarity threshold. The estimated efficacy may be presented in the form of an alphanumeric value or a color, to name a few examples.

At step 808, the EMG system 30 may derive an intra-uterine measurement based on the EMG signals, either in their raw or processed formats. This is due to the pelvic floor muscles being a short distance from the other side of the perineum, as well as the additional weight of the uterus during pregnancy (e.g., ten to twenty times heavier than normal for the patient 10) that, together with the weight of the child 12 bearing down, combine to push the uterus closer to the pelvic floor during delivery. Thus, either from picking up uterine muscle electrical activity due in addition to pelvic floor muscle measurements, or from deriving a uterine value during processing, uterine measurements may also be provided according to embodiments of the present disclosure, e.g. to provide information about when contractions are occurring in order to assist with voluntary pushing efforts.

At step 810, the EMG system 30 may take one or more of the pelvic floor signals and the uterine measurements to predict a likelihood of success of vaginal birth based on the estimated efficacy of pushing. From this data, the medical staff may coach the patient 10 on different pushing methods, or intensity of pushing, at efficacious times such as during a uterine contraction, as well as use the prediction as a factor to assist in deciding whether labor is stalled and/or that a Cesarean section is otherwise necessary or advisable.

If at decision step 812 labor is not done (e.g., child 12 has not exited the birth canal), the method 800 may loop back again to proceed with step 804 until it is stopped because the child has either exited the birth canal or medical staff have determined to perform a Cesarean section instead, e.g. based on the prediction and/or other data presented via aspects of the labor monitoring system 100.

If at decision step 812 labor is done (or the decision has been made to perform a Cesarean), the EMG sensors are removed at step 814.

Figure 9:
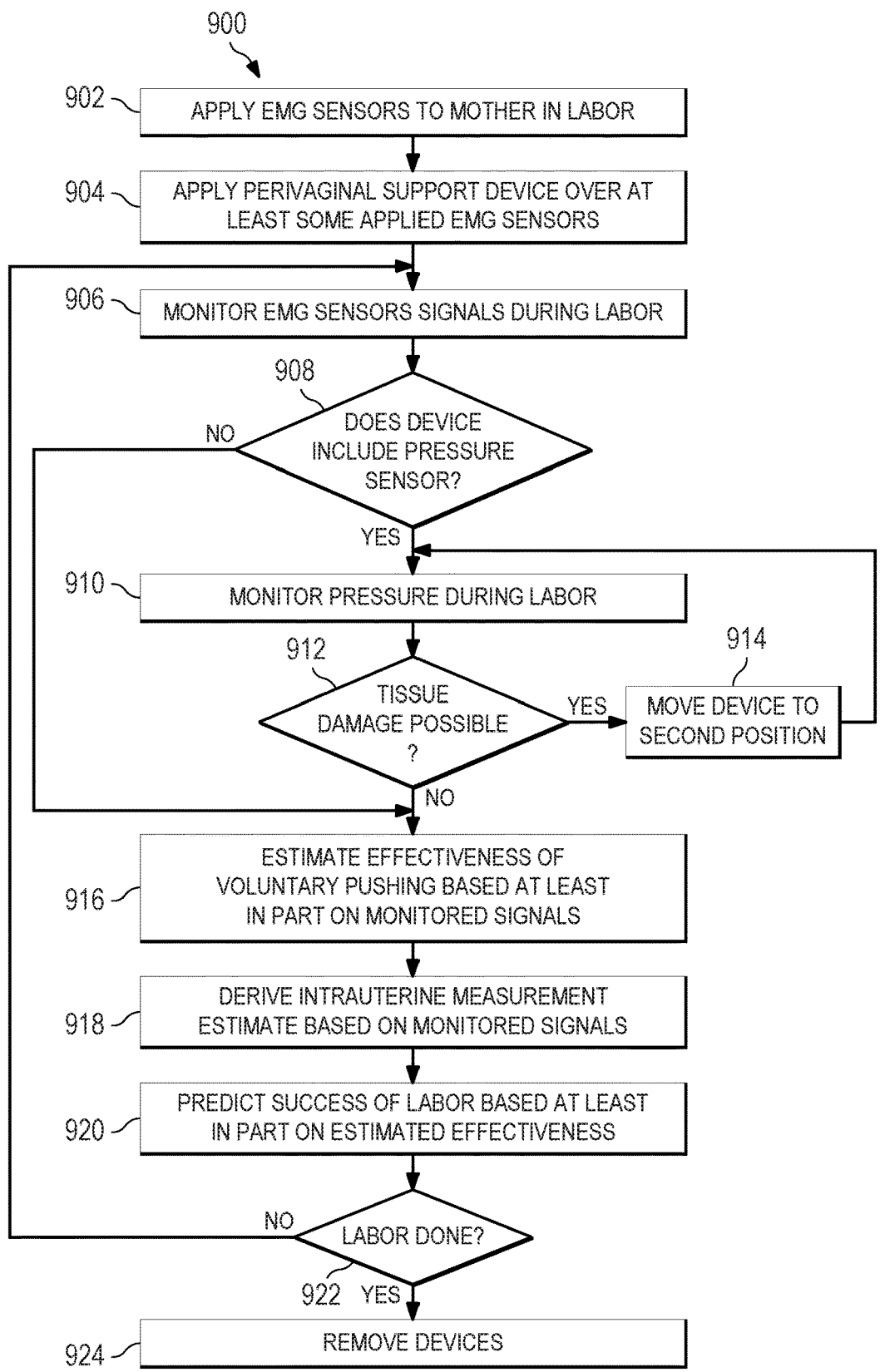
FIG. 9 illustrates a method of managing a mother's child birthing labor according to an exemplary embodiment.

FIG. 9 illustrates a method 900 of managing a mother's child birthing labor according to an exemplary embodiment. In an embodiment, the method 900 is an exemplary method with respect to the patient 10 discussed above with respect to FIGS. 1 and 2 specifically while using the EMG system 30 discussed with respect to FIG. 4 in cooperation with a perivaginal support device 101 such as in the examples of FIGS. 5A and 5B above.

At step 902, medical staff apply one or more EMG sensors 420 to a patient in labor, for example some time before or at the start of stage II labor, for example as described above with respect to step 802 of FIG. 8.

At step 904, medical staff apply a perivaginal support device 101 behind at least some of the applied EMG sensors 420. This may be done, for example, as described above with respect to FIGS. 5A and 5B. In one aspect, the perivaginal support device 101 is advanced inwardly toward the pelvic floor muscles to push the EMG sensors 420 closer to the muscles. In one form, the perivaginal support device 101 is advanced until EMG signals above a minimum threshold are detected. The perivaginal support device 101 may be secured in place to maintain the relative position of the sensors 420 to the pelvic floor muscles. With the perivaginal support device 101 applied behind at least some EMG sensors 420, those EMG sensors 420 are further held in place by the pressure applied by the perivaginal support device 101.

At step 906, the EMG system 30 monitors signals produced and received from the EMG sensors 420 during labor, for example as discussed above with respect to step 804 of FIG. 8.

At decision step 908, if the perivaginal support device 101 includes a pressure detection system 250, the method 900 proceeds to step 910.

At step 910, the labor monitoring and support system 100 monitors the pressure detected by the pressure detection system 250 during labor. In an embodiment, the pressure detection system 250 may send its detected values to the EMG system 30 directly for analysis or, alternatively, to a separate computing device. Where a separate computing device is used, the separate computing device may either transmit its data to the EMG system 30, or vice versa, or each to a third computing device, for analysis and presentation to a user.

At decision step 912, if tissue damage is possible, the method 900 proceeds to step 914, where the perivaginal support device 101 is repositioned so as to reduce the amount of pressure to a safer level. This may take the form of a warning sound, a light turning on or changing color, or a presentation on a graphical user interface of a display that a user, such as medical staff, may see and respond to by making the adjustment. In an embodiment, a system monitoring the pressure data determines that tissue damage is possible by comparing the pressure values with one or more of a pressure amount threshold, or pressure time duration threshold, or some combination of the above to name just a few examples.

Once the adjustment is performed at step 914, the method 900 loops back to step 910 to continue monitoring pressure.

Returning to decision step 912, if tissue damage is not likely possible, again for example as determined by one or more comparisons to one or more thresholds at a computing device, then method 900 proceeds to step 916.

At step 916, the EMG system 30 estimates an effectiveness of voluntary pushing by the patient 10 based on the monitored and processed EMG signals received from the EMG sensors 420. In addition to the comparisons discussed above with respect to FIG. 8's method 800, the EMG system 30 (or some third computing device) may utilize both the EMG values and any pressure values from the pressure detection system 250 in determining effectiveness of voluntary pushing, for example by combining the results of threshold comparisons of both EMG signal values and pressure values. Additionally or alternatively, the results from comparing the EMG signal values to a library of values may be combined in a weighted or non-weighted manner with the pressure value comparisons to result in an estimated efficacy of voluntary pushing.

At step 918, the EMG system 30 may derive an intrauterine measurement based on the EMG signals, either in their raw or processed formats, for example as discussed with respect to step 808 of FIG. 8 above.

At step 920, the EMG system 30 may take one or more of the pelvic floor signals, the uterine measurements, and pressure values to predict a likelihood of success of vaginal birth based on the estimated efficacy of pushing. From this data, the medical staff may coach the patient 10 on different pushing methods, or intensity of pushing, at efficacious times such as during a uterine contraction, as well as use the prediction as a factor to assist in deciding whether labor is stalled or that a Cesarean section is otherwise necessary or advisable.

At decision step 922, if labor is not done (e.g., child 12 has not exited the birth canal), the method 900 may loop back again to proceed with step 906 until it is stopped because the child has either exited the birth canal or medical staff have determined to perform a Cesarean section instead, e.g. based on the prediction and/or other data presented via aspects of the labor monitoring system 100. If labor is done or the decision has been made to perform a Cesarean, the EMG sensors and perivaginal support device 101 are removed at step 924.

Returning to decision step 908, if the perivaginal support device 101 does not include a pressure detection system 250, the method 900 proceeds directly to step 916 as discussed above and as described with respect to method 800 of FIG. 8 above.

In an embodiment, the monitoring of pressure from the perivaginal support device 101 is ongoing at the same time as the monitoring of the EMG signals, so that while EMG signals are being monitored and analyzed the perivaginal support device 101 may still be adjusted to counter against any possible tissue damage.

Figure 10:
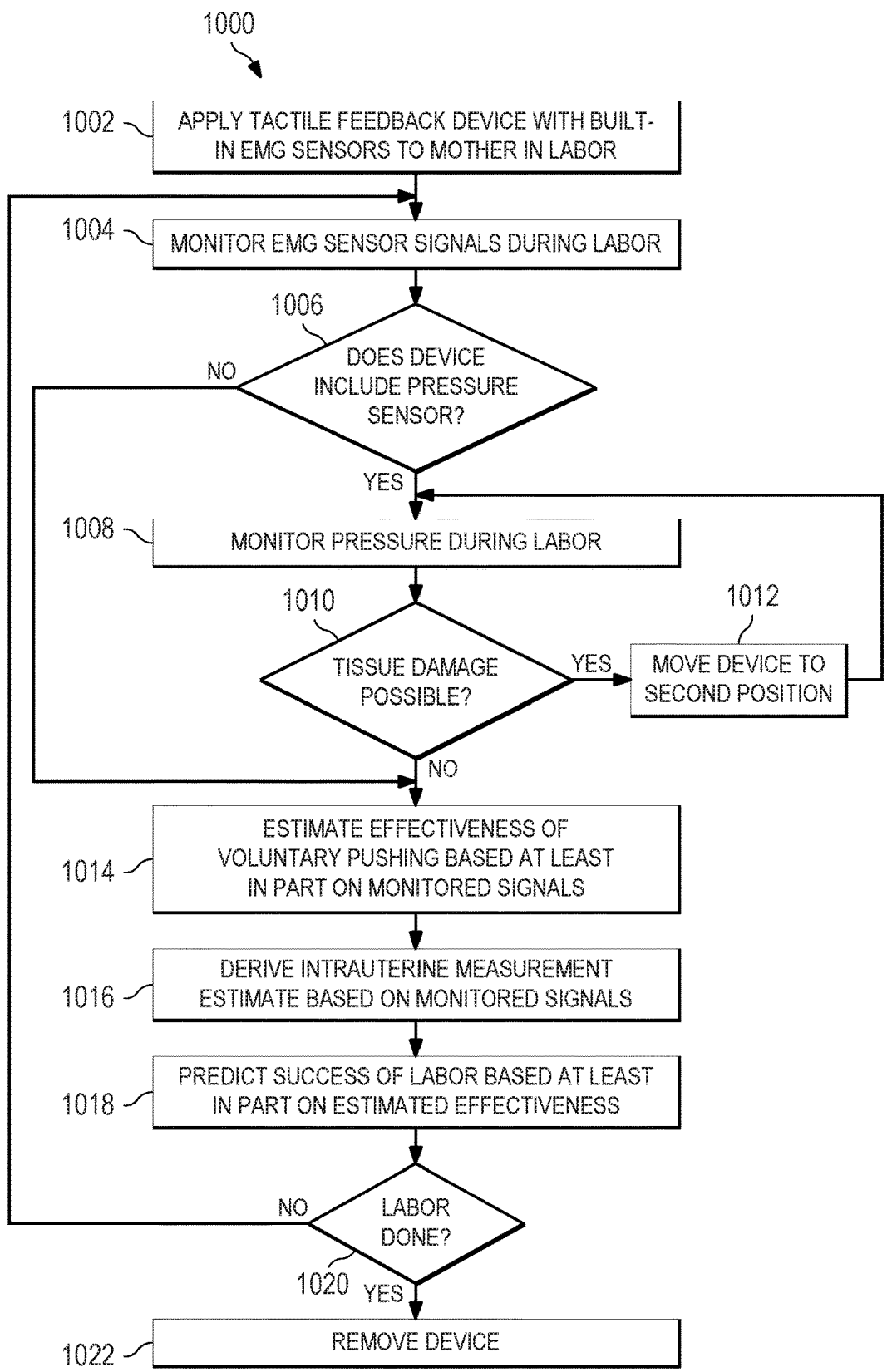
FIG. 10 illustrates a method of managing a mother's child birthing labor according to an exemplary embodiment.

FIG. 10 illustrates a method of managing a mother's child birthing labor according to an exemplary embodiment. In an embodiment, the method 1000 is an exemplary method with respect to the patient 10 discussed above with respect to FIGS. 1 and 2 specifically while using an EMG system 30 with EMG sensors attached to or combined with a perivaginal support device 101 such as in the examples of FIGS. 6A, 6B, 7A, and 7B above.

At step 1002, medical staff apply a perivaginal support device 101 that has one or more EMG sensors attached to or integrated with the device to a perivaginal region of the patient 10, for example as described above with respect to FIGS. 5A and 5B. Where the perivaginal support device 101 is according to the embodiments of FIGS. 6A and 6B, at least some subset of the EMG sensors in the EMG sensor arrays 602, 604, and 606 are placed over muscles in the pelvic floor region that are of interest for monitoring. Similarly, where the perivaginal support device 101 is according to the embodiments of FIGS. 7A and 7B, at least some subset of the EMG sensors located throughout the perivaginal support device 101 are placed over muscles in the pelvic floor region that are of interest for monitoring.

At step 1004, the EMG system 30 monitors signals produced and received from the EMG sensors (e.g., the sensor arrays of FIGS. 6A and 6B or the sensors depicted in FIGS. 7A and 7B) during labor, for example as discussed above with respect to step 804 of FIG. 8. In an embodiment, a filter may be included either with the electrodes of the EMG sensors or at the EMG system 30 that may filter out signals from EMG sensors in the arrays that are not placed over muscles, for example by filtering out EMG signals that fall below a specified threshold or by some other metric as will be recognized by those skilled in the relevant art(s). The EMG signals output from embodiments of FIGS. 7A and 7B may also be filtered so that only those signals are used that reflect muscles of the pelvic floor region.

At decision step 1006, if the perivaginal support device 101 with attached/integrated EMG sensors includes a pressure detection system 250, the method 1000 proceeds to step 1008.

At step 1008, the labor monitoring and support system 100 monitors the pressure detected by the pressure detection system 250 during labor, for example as discussed above with respect to step 910 of FIG. 9.

At decision step 1010, if tissue damage is possible, the method 1000 proceeds to step 1012, where the perivaginal support device 101 is repositioned so as to reduce the amount of pressure to a safer level, for example as discussed above with respect to step 914 of FIG. 9.

Once the adjustment is performed at step 1012, the method 1000 loops back to step 1008 to continue monitoring pressure.

Returning to decision step 1010, if tissue damage is not likely possible, again for example as determined by one or more comparisons to one or more thresholds at a computing device, then method 1000 proceeds to step 1014.

At step 1014, the EMG system 30 estimates an effectiveness of voluntary pushing by the patient 10 based on the monitored and processed EMG signals received from the EMG sensors attached to or integrated with the perivaginal support device 101. In addition to the comparisons discussed above with respect to FIG. 8's method 800, the EMG system 30 (or some third computing device) may utilize both the EMG values and any pressure values from the pressure detection system 250 in determining effectiveness of voluntary pushing, such as described with respect to step 916 of FIG. 9 above.

At step 1016, the EMG system 30 may derive an intrauterine measurement based on the EMG signals, either in their raw or processed formats, for example as discussed with respect to step 808 of FIG. 8 above.

At step 1018, the EMG system 30 may take one or more of the pelvic floor signals, the uterine measurements, and pressure values to predict a likelihood of success of vaginal birth based on the estimated efficacy of pushing. From this data, the medical staff may coach the patient 10 on different pushing methods, or intensity of pushing, at efficacious times such as during a uterine contraction, as well as use the prediction as a factor to assist in deciding whether labor is stalled or that a Cesarean section is otherwise necessary or advisable.

At decision step 1020, if labor is not done (e.g., child 12 has not exited the birth canal), the method 1000 may loop back again to proceed with step 1004 until it is stopped because the child has either exited the birth canal or medical staff have determined to perform a Cesarean section instead, e.g. based on the prediction and/or other data presented via aspects of the labor monitoring system 100. If labor is done or the decision has been made to perform a Cesarean, the perivaginal support device 101 with attached/integrated EMG sensors is removed at step 1022.

Returning to decision step 1006, if the perivaginal support device 101 does not include a pressure detection system 250, the method 1000 proceeds directly to step 1014 as discussed above.

In an embodiment, the monitoring of pressure from the perivaginal support device 101 is ongoing at the same time as the monitoring of the EMG signals, so that while EMG signals are being monitored and analyzed the perivaginal support device 101 may still be adjusted to counter against any possible tissue damage.

Embodiments of the present disclosure contemplate a kit that may include one or more of the components described above provided in a package. In one embodiment, the kit includes at least sterilized EMG sensors. In another aspect, the kit includes a sterilized perivaginal support device. In another aspect, the kit further includes an anchoring assembly as described above. In another aspect, the kit includes a pressure detecting system. In another aspect, the kit includes a patient adjustment system. In another aspect, the kit includes a sterilized perivaginal support device with one or more EMG sensors built in with the device, with or without a pressure detecting system. In some embodiments, the anchoring assembly may be preassembled with the perivaginal support device as shown in the drawings or may be provided unassembled. In the unassembled kit, medical staff will remove the support device and anchoring assembly from the packaging and assemble the support device with the anchoring assembly and the pressure detecting system. As set forth above, the anchoring assembly may be adhered to the support assembly near the patient or the support assembly may include fastening members or apertures to receive elements of the anchoring assembly. For example, the support device may include an aperture and a portion of a flexible strap may be threaded through the aperture to join the two components. In still a further embodiment, the kit includes a treating compound to apply to the patient. In one such embodiment, the treating compound is provided in a separate package. In an alternative embodiment, the treating compound is applied to or incorporated into the support device on the perivaginal contact surface.

Perivaginal monitoring and support devices as described herein may be applied to patients for a variety of reasons including, alone or in combination, any of the following: a) shortening second stage labor by providing feedback regarding the efficacy of voluntary pushing efforts to enhance the effectiveness of contractions in advancing the baby down the birth canal; b) shortening second stage labor by providing a push focal point to enhance the effectiveness of contractions in advancing the baby down the birth canal; c) reducing the necessity of Cesarean section births by encouraging and monitoring, via EMG data and, in some embodiments, pressure feedback, the effectiveness of contractions and voluntary pushing to generate a pushing effect on the baby to move it toward the vaginal opening as sensed by muscle contractions and pressure exerted on the perivaginal tissue; d) covering all or most of the anal orifice and thereby providing defecation control; e) suppressing hemorrhoid development and/or advancement of existing hemorrhoids; and f) delivering post-delivery therapeutic treatments, such cooling treatments, for example.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure. Furthermore, although elements of the described embodiments may be described or claimed in the singular, the plural is contemplated unless limitation to the singular is explicitly stated. Additionally, all or a portion of any aspect and/or embodiment may be utilized with all or a portion of any other aspect and/or embodiment.

What is claimed is:

1. A child birth labor apparatus, comprising:
an electrode configured for placement adjacent a pelvic floor of a patient in childbirth labor, the electrode configured to detect an electrical signal from a tissue of the pelvic floor and output the detected electrical signal;

a perivaginal support member comprising a tissue contact surface configured to contact tissue of a perivaginal region of the pelvic floor where the electrode is placed;

a computing system configured to receive the electrical signal from the electrode and a processor configured to analyze the electrical signal from the tissue of the pelvic floor to estimate an efficacy of voluntary pushing by the patient; and a user interface coupled to the computing system and configured to present information relating to the estimated efficacy of voluntary pushing by the patient.

2. The child birth labor apparatus of claim 1, wherein the perivaginal support member further comprises:

a side contact portion coupled with the tissue contact surface and comprising a first surface disposed to face a first buttock in a gluteal cleft of the patient and a second surface disposed to face a second buttock in the gluteal cleft of the patient when the tissue contact surface is disposed adjacent an anal orifice of the patient.

3. The child birth labor apparatus of claim 2, wherein:

the tissue contact surface is configured to apply pressure to the contacted tissue of the perivaginal region, and the side contact portion is configured to convey an applied load to the tissue contact surface.

4. The child birth labor apparatus of claim 1, wherein the perivaginal support member is placed behind the electrode and applies pressure to the electrode in order to maintain placement of the electrode.

5. The child birth labor apparatus of claim 4, wherein the perivaginal support member comprises a pressure sensor, the pressure sensor configured to detect pressure applied by tissue of the perivaginal region on the perivaginal support member.

6. The child birth labor apparatus of claim 1, wherein the perivaginal support member comprises the electrode, the electrode being integrated with the tissue contact surface.

7. The child birth labor apparatus of claim 6, wherein the electrode is placed adjacent to at least one of a transverse perineal muscle or a levator ani muscle.

8. The child birth labor apparatus of claim 1, wherein the computing system is configured to estimate the efficacy of the voluntary pushing by comparing a metric related to the electrical signal with a predetermined threshold.

9. The child birth labor apparatus of claim 1, wherein the electrode comprises a plurality of electrodes, comprising:

a first electrode from among the plurality of electrodes placed adjacent to a transverse perineal muscle, the first electrode configured to detect an electrical signal generated by an electrical potential at the transverse perineal muscle; and a second electrode from among the plurality of electrodes placed adjacent to a levator ani muscle, the second electrode configured to detect an electrical signal generated by an electrical potential at the levator ani muscle.

10. The child birth labor apparatus of claim 1, wherein the electrode comprises a surface electrode.

11. A child birth labor apparatus, comprising:

an electrode configured for placement adjacent a pelvic floor of a mother in childbirth labor, the electrode configured to detect an electrical signal from a tissue of the pelvic floor and output the detected electrical signal;

a perivaginal support member comprising a tissue contact surface configured to contact tissue of the pelvic floor where the electrode is placed; and a computing system configured to receive the electrical signal from the electrode and analyze the electrical signal to estimate an efficacy of voluntary pushing by the mother.

12. The child birth labor apparatus of claim 11, wherein the perivaginal support member further comprises a side contact portion comprising a first surface disposed to face a first buttock in a gluteal cleft of the mother and a second surface disposed to face a second buttock in the gluteal cleft of the mother when the tissue contact surface is disposed adjacent an anal orifice of the mother.

13. The child birth labor apparatus of claim 12, wherein:

the tissue contact surface is configured to apply pressure to the contacted tissue of the pelvic floor, and the side contact portion is configured to convey an applied load to the tissue contact surface.

14. The child birth labor apparatus of claim 11, wherein the perivaginal support member is placed behind the electrode and applies pressure to the electrode in order to maintain placement of the electrode.

15. The child birth labor apparatus of claim 11, wherein the perivaginal support member comprises a pressure sensor, the pressure sensor configured to detect pressure applied by tissue of the pelvic floor on the perivaginal support member.

16. The child birth labor apparatus of claim 11, wherein the perivaginal support member further comprises a side contact portion, and the electrode is integrated with at least one of the tissue contact surface and the side contact portion.

17. The child birth labor apparatus of claim 11, wherein the electrode comprises a plurality of electrodes, comprising:

a first electrode from among the plurality of electrodes placed adjacent to a transverse perineal muscle, the first electrode configured to detect an electrical signal generated at the transverse perineal muscle; and a second electrode from among the plurality of electrodes placed adjacent to a levator ani muscle, the second electrode configured to detect an electrical signal generated at the levator ani muscle.

18. A method, comprising:

placing a perivaginal support member over an electrode adjacent to a pelvic floor of a patient in childbirth labor;

applying, with the perivaginal support member, pressure on tissue of the pelvic floor where the electrode is placed;

receiving, at a computing system, an electrical signal generated from the electrode placed adjacent to the pelvic floor;

analyzing, by the computing system, the electrical signal to estimate an efficacy of voluntary pushing by the patient; and presenting, from the computing system, information relating to the estimated efficacy of voluntary pushing by the patient.

19. The method of claim 18, further comprising:

deriving an intrauterine measurement of the patient based at least in part on the electrical signal from the electrode; and predicting whether the childbirth labor will be successful based at least in part on the estimated efficacy of the voluntary pushing, wherein the prediction is used to determine whether a cesarean section is necessary.

20. The method of claim 18, wherein the perivaginal support member comprises a pressure sensor, the method further comprising:

detecting, by the pressure sensor, an amount of pressure applied by the tissue of the pelvic floor on the perivaginal support member, wherein the analyzing to estimate the efficacy of the voluntary pushing further comprises:
determining, based on the detected amount of pressure in cooperation with the analysis of the electrical signal, whether the voluntary pushing meets a threshold corresponding to successful pushing.

* * * * *